(12) United States Patent
Zhao et al.

(10) Patent No.: US 6,939,451 B2
(45) Date of Patent: Sep. 6, 2005

(54) MICROFLUIDIC CHIP HAVING INTEGRATED ELECTRODES

(75) Inventors: Mingqi Zhao, Cupertino, CA (US); Petr Vanysek, DeKalb, IL (US); Antonio Ricco, Los Gatos, CA (US); Hilary S. Lackritz, Cupertino, CA (US); Zhu Qun, Mountain View, CA (US); Uyen Nguyen, San Jose, CA (US); Torleif O. Bjornson, Gilroy, CA (US)

(73) Assignee: Aclara Biosciences, Inc., Mountain View, CA (US)

( * ) Notice: Subject to any disclaimer, the term of this patent is extended or adjusted under 35 U.S.C. 154(b) by 466 days.

(21) Appl. No.: 09/939,327

(22) Filed: Aug. 24, 2001

(65) Prior Publication Data

US 2002/0079219 A1 Jun. 27, 2002

Related U.S. Application Data

(60) Provisional application No. 60/233,838, filed on Sep. 19, 2000.

(51) Int. Cl.$^7$ ............................ G01N 27/447; B32B 7/00
(52) U.S. Cl. ....................... 204/451; 204/454; 204/601; 422/99; 422/101; 422/68.1; 435/288.4; 435/288.5; 435/287.1; 435/287.3
(58) Field of Search ................................. 204/451, 454, 204/601; 422/99, 101, 68.1; 435/288.4, 288.5, 287.1, 287.3

(56) References Cited

U.S. PATENT DOCUMENTS

| | | | |
|---|---|---|---|
| 2,772,322 A | 11/1956 | Witt et al. | |
| 2,940,830 A | 6/1960 | Thornhill | |
| 3,351,495 A | 11/1967 | Larson | |
| 3,696,061 A | 10/1972 | Selsor et al. | |

(Continued)

FOREIGN PATENT DOCUMENTS

| | | |
|---|---|---|
| AT | 404 099 | 8/1998 |
| EP | 0107631 | 5/1984 |
| EP | 0376611 | 7/1990 |
| EP | 0620432 | 10/1994 |
| GB | 2191110 | 12/1987 |
| GB | 2204270 | 11/1988 |
| WO | WO 91/16966 | 11/1991 |
| WO | WO 96/04547 | 2/1996 |
| WO | WO 98/45693 | 10/1998 |
| WO | WO 99/19717 | 4/1999 |

OTHER PUBLICATIONS

U.S. App. No. 60/239,305, filed Oct. 10, 2000.*

Bart, S.F. et al. (1990). "Microfabricated electrohydrodynamic pumps," *Sensors and Actuators* A21–A23:193–197.

(Continued)

*Primary Examiner*—Alan Diamond
(74) *Attorney, Agent, or Firm*—Stephen C. Macevicz; David Albagli

(57) ABSTRACT

A microfluidic device having integrated components for conducting chemical operations. Depending upon the desired application, the components include electrodes for manipulating charged entities, heaters, electrochemical detectors, sensors for temperature, pH, fluid flow, and other useful components. The device may be fabricated from a plastic substrate such as, for example, a substantially saturated norbornene based polymer. The components are integrated into the device by adhering an electrically conductive film to the substrate. The film may be made of metal or an electrically conducting ink and is applied to the device through metal deposition, printing, or other methods for applying films. Methods for reducing bubble formation during electrokinetic separation and methods for heating material in a microfluidic device are also disclosed.

20 Claims, 19 Drawing Sheets

U.S. PATENT DOCUMENTS

| | | | |
|---|---|---|---|
| 3,725,520 A | | 4/1973 | Suzuki et al. |
| 3,862,030 A | | 1/1975 | Goldberg |
| 3,903,234 A | | 9/1975 | Ikeda et al. |
| 3,967,978 A | | 7/1976 | Honda et al. |
| 4,024,323 A | | 5/1977 | Versteegh |
| 4,102,746 A | | 7/1978 | Goldberg |
| 4,169,014 A | | 9/1979 | Goldberg |
| 4,210,709 A | | 7/1980 | Doi et al. |
| 4,226,926 A | | 10/1980 | Goldberg et al. |
| 4,237,083 A | | 12/1980 | Young et al. |
| 4,335,193 A | | 6/1982 | Doi et al. |
| 4,350,655 A | | 9/1982 | Hoge |
| 4,472,328 A | | 9/1984 | Sugimoto et al. |
| 4,585,604 A | | 4/1986 | Okuyama et al. |
| 4,597,828 A | | 7/1986 | Tadros |
| 4,613,643 A | | 9/1986 | Nakamura et al. |
| 4,648,417 A | | 3/1987 | Johnson et al. |
| 4,681,750 A | | 7/1987 | Johnson et al. |
| 4,734,229 A | | 3/1988 | Johnson et al. |
| 4,759,986 A | | 7/1988 | Marikar et al. |
| 4,765,864 A | | 8/1988 | Holland et al. |
| 4,791,144 A | | 12/1988 | Nagou et al. |
| 4,833,172 A | | 5/1989 | Schwarz et al. |
| 4,861,644 A | | 8/1989 | Young et al. |
| 4,868,008 A | | 9/1989 | Marikar et al. |
| 4,874,500 A | | 10/1989 | Madou et al. |
| 4,908,112 A | | 3/1990 | Pace |
| 4,945,135 A | | 7/1990 | Grubbs et al. |
| 5,047,283 A | | 9/1991 | Leatherman et al. |
| 5,126,022 A | | 6/1992 | Soane et al. |
| 5,191,026 A | | 3/1993 | Nishi et al. |
| 5,198,511 A | | 3/1993 | Brown Wensley et al. |
| 5,312,940 A | | 5/1994 | Grubbs et al. |
| 5,342,909 A | | 8/1994 | Grubbs et al. |
| 5,362,307 A | * | 11/1994 | Guy et al. .................... 604/20 |
| 5,498,392 A | | 3/1996 | Wilding et al. |
| 5,565,143 A | * | 10/1996 | Chan .......................... 252/514 |
| 5,571,410 A | | 11/1996 | Swedberg et al. |
| 5,585,069 A | | 12/1996 | Zanzucchi et al. |
| 5,587,128 A | | 12/1996 | Wilding et al. |
| 5,599,432 A | | 2/1997 | Manz et al. |
| 5,603,351 A | | 2/1997 | Cherukuri et al. |
| 5,605,662 A | | 2/1997 | Heller et al. |
| 5,630,924 A | | 5/1997 | Fuchs et al. |
| 5,635,358 A | | 6/1997 | Wilding et al. |
| 5,637,469 A | | 6/1997 | Wilding et al. |
| 5,705,813 A | | 1/1998 | Apffel et al. |
| 5,716,825 A | | 2/1998 | Hancock et al. |
| 5,750,015 A | | 5/1998 | Soane et al. |
| 5,792,943 A | | 8/1998 | Craig |
| 5,858,187 A | | 1/1999 | Ramsey et al. |
| 5,858,188 A | | 1/1999 | Soane et al. |
| 5,858,195 A | | 1/1999 | Ramsey |
| 5,861,242 A | | 1/1999 | Chee et al. |
| 5,900,130 A | | 5/1999 | Benvegnu et al. |
| 5,906,723 A | | 5/1999 | Mathies et al. |
| 5,942,443 A | | 8/1999 | Parce et al. |
| 5,992,820 A | | 11/1999 | Fare et al. |
| 6,010,607 A | | 1/2000 | Ramsey |
| 6,024,854 A | | 2/2000 | Gilchrist |
| 6,033,546 A | | 3/2000 | Ramsey |
| 6,063,589 A | | 5/2000 | Kellogg et al. |
| 6,099,939 A | | 8/2000 | Mittal et al. |
| 6,103,199 A | * | 8/2000 | Bjornson et al. ........... 422/100 |
| 6,284,113 B1 | * | 9/2001 | Bjornson et al. ........... 204/453 |
| 6,375,871 B1 | * | 4/2002 | Bentsen et al. ............. 264/1.6 |
| 6,623,860 B2 | * | 9/2003 | Hu et al. .................. 428/411.1 |
| 2002/0092767 A1 | * | 7/2002 | Bjornson et al. ........... 204/451 |
| 2002/0122747 A1 | * | 9/2002 | Zhao et al. .................... 422/99 |
| 2004/0018297 A1 | * | 1/2004 | Davidson et al. ............. 427/58 |

OTHER PUBLICATIONS

Bergveld, P. (1994). "The challenge of developing $\mu$–tas," in *Micro Total Analysis Systems* A. Van Den Berg and P. Bergveld (eds.), MESA research Institute. pp. 1–4.

Burns, M.A. et al. (1996). "Microfabricated structures for integrated DNA analysis," *Proc. Natl. Acad. Sci. USA* 93:5556–5561.

Effenhauser, C. S. et al. (1997). "Integrated Chip–based Capillary Electrophoresis," *Electrophoresis* 18:2203–2213.

Elwenspoek, M. et al. (1994). "Towards Integrated Microliquid Handling Systems," *J. Micromech. Microeng.* 4:227–245.

Fan, Z. (1994). "Micromachining, Capillary Electrophoresis, Polymers, and Their Applications to Chemical Sensors," *University of Alberta Graduate Thesis.* pp. 1–210.

Fuhr, G. et al. (1994). "Travelling wave–driven microfabricated electrohydrodynamic pumps for liquids," *J. Micromech. Microeng.* 4:217–226.

Gravesen, P. et al. (1993). "Microfluidics–a review," *J. Micromech. Microeng.* 3:168–182.

Kumar, A. et al. (1993). "Features of gold having micrometer to centimeter dimensions can be formed through a combination of stamping with an elastomeric stamp and an alkaethiol "ink" followed by chemical etching," *Appl. Phys. Lett.* 63(14):2002–2004.

Kumar, A. et al. (1994). "Patterning self–assembled monolayers: Applications in materials science," *Langmuir.* 10(5):1498–1511.

Lammerink, T.S.J. et al. (1996). Modular concept for fluid handling systems, Ninth Intl Workshop on Micro Electro Mech Sys, IEEE. pp. 389–399.

Manz, A. et al. (1990). "Design of an open–tubular column liquid chromatograph using silicon chip technology," *Sensors and Actuators* B1:249–255.

Manz, A. et al. (1991). "Integrated electroosmotic pumps and flow manifolds for total chemical analysis systems," *Digest of Transducers '91; Proc of IEEE..* pp. 939–942.

Manz, A. et al. (1995). "$\mu$–Tas: Miniaturized total chemical analysis systems," in *Micro Total Analysis Systems.* A. Van Den Berg and P. Bergveld (eds.) Kluwer Academic Publishers. pp. 5–27.

McCormick, R.M. et al. (1997). "Microchannel Electrophoretic Separations of DNA in Injection–Molded Plastic Substrates," *Anal. Chem.* 69:2626.

Menon, V.P. et al. (1995). "Fabrication and Evaluation of Nanoelectrode Ensembles," *Analytical Chemistry* 67(13):1920–1928.

Mittal K.L. ed. (1989). *Metallized Plastics. Fundamentals and Applications.* Marcel Dekker, Inc:New York. (Table of Contents only).

Northrup, M.A. et al. (1993). "DNA Amplification with a Fabricated Reaction Chamber," *The 7th International Conference on Solid–State Sensors and Actuators* Jun. 7–10. pp. 924–926.

Richter, A. et al. (1991). "A micromachined electrohydrodynamic (EHD) pump," *Sensors and Actuators* A29:159–168.

Richter, A. et al. (1991). "Electrohydrodynamic pumping and flow measurement," *MEMS '91; Proc. IEEE*.

Ružička, J. et al. (1994). "Integrated microconduits for flow injection analysis," *Analytica Chimica Acta* 161:1–25.

Schut, J.H. (2000). "New Cyclic Olefins are Clearly Worth a Look," *Plastic Technology* 46(3):44 and 46.

Shoji, S. et al. (1994). "Microflow devices and systems," *J. Micromech. & Microeng.* 4:157–171.

Thormann, W. et al. (1984). "Detection of transient and steady states in electrophoresis: Description and applications of a new apparatus with 255 potential gradient detectors along the separation trough," *Electrophoresis* 5:323–337.

Verpoorte, E.M. et al. (1994). "Three–dimensional micro flow manifolds for miniaturized chemical analysis systems," *J. Micromech. Microeng.* 4:246–256.

Washizu, M. et al. (1987). "Novel method of cell fusion in field constriction area in fluid integrated circuit," *Conference Record of IEEE/IAS.* pp. 1549–1553.

Wilbur, J.L. et al. (1994). "Microfabrication by microcontact printing of self–assembled monolayers," *Adv. Materials* 6(7/8):600–604.

Woods, A.S. (1988). "Film and Design Developments Power a Buildup in Flexible Circuitry," *Modern Plastics* Dec., pp. 73–75.

Wood, A.S. (1988). "Molded 3–D Circuit Boards: Market Takeoff Coming in 1989," *Modern Plastics* Dec., pp. 64–71.

Wood, F. et al. (1989). "Two New Processes Make Circuitry a Part of the Part," *Research & Development* pp. 71, 72 and 74.

Woolley, A.T. et al. (1996). "Functional integration of PCR amplification and capillary electrophoresis in a microfabricated DNA analysis device," *Analytical Chemistry* 68(23):4081–4086.

Zhao, M. et al. (2000). "Distribution and Mixing of Reagent on Multichannel Plastic Chips," in *Technical Digest of the 2000 Solid–State Sensor and Actuator Workshop.* Transducers Research Foundation: Cleveland. pp. 183–186.

Hashimoto, M. (1997). "Synthesis and Properties of Hydrogenated Ring Opening Metathesis Polymer," *Polymeric Materials: Science and Engineering, American Chemical Society* 76: 61.

Bianchi, F. et al. (1998). "Photoablated Micro–Structures for Electrophoresis," *Nanotech '98, Ecole Polytechnique de Lausanne*, 18 pages.

Northrup, M.A. et al. (Jan. 25–28, 1993). "DNA Amplification with a Microfabricated Reaction Chamber," *The 7th International Converence on Solid–State Sensors and Actuators,* Digest of Technical Papers, Transducers '93, Jun. 7–10, 1993, Pacifico, Yokohama, Japan, pp. 924–926.

Reymond, F. et al. (1999). "Electrochemical Sensor Research at the Laboratoire d'Electrochimie of the EPFL," *Chimia* 53(3):103–108.

Rossier, J.S. et al. (1997). "Electrode Materials Generated by Scanning UV–Laser Deposition from Polystyrene," *Electrochemical Society Proceedings,* Paris, France, p. 826, abstract No. 703.

Rossier, J.S. (1999a). "Photoablated Polymer Microsystems for Electro– and Biochemical Analyses," *Ph.D. Thesis NR 2102, Ecole Polytechnique Federale de Lausannne, Switzerland,* located at <http://dcwww.epfl.ch/le/ICP3–Theses/ICP3–Rossier.html> on Nov. 5, 2002, 168 pages.

Rossier, J.S. et al. (1999b). "Electrochemical Detection in Polymer Microchannels," *Anal. Chem.* 71(19):4294–4299.

Rossier, J.S. et al. (1999c). "Microchannel Networks for Electrophoretic Separations," *Electrophoresis* 20:727–731.

Rossier, J.S. et al. (1999d). "Nanocrysalline Carbon Film Electrodes Generated and Patterned by UV–Laser Ablation of Polystyrene," *Phys. Chem. Chem. Phys.* 1:3647–3652.

Rossier, J.S. et al. (2000) "Electrophoresis with Electrochemical Detection in a Polymer Microdevice," *J. Electroanal. Chem.* 492:15–22.

Rossier, J.S. et al. (2001). "Enzyme Linked Immunosorbent Assay on a Microchip with Electrochemcial Detection," *Lab on a Chip* 1:153–157.

Schwarz, A. et al. (1998). "Micro–TAS on Polymer Substrates Micromachined by Laser Photoablation," *in Proccedings of the TAS'98 Workshop Held in Banff,* Canada, Oct. 13–16, 1998. Harrson D.J and A. van den Berg (eds.). Kluwer Academic Publishers: Dordrecht. pp. 241–244.

Wolley, A.T. et al. (1998). "Capillary Electrophoesis Chips with Integrated Electrochemical Detection," *Anal. Chem.* 70(4):684–688.

* cited by examiner

| eTag Probes (-FC) | Migration Time (min) | | | | Normalized Peak Height | | | | Half Peak Width | | | | Resolution | | | |
|---|---|---|---|---|---|---|---|---|---|---|---|---|---|---|---|---|
| | Average | | CV | | Average | | CV | | Average | | CV | | Average | | CV | |
| | Pt | Ink | Pt | Ink | Pt | Ink | Pt | Ink | Pt | Ink | Pt | Ink | Pt | Ink | Pt | Ink |
| 163 | 1.56 | 1.50 | 6.61 | 0.19 | 0.69 | 0.56 | 2.81 | 4.74 | 0.15 | 0.12 | 33.81 | 4.60 | | | | |
| 158 | 1.58 | 1.51 | 6.80 | 0.19 | 0.27 | 0.22 | 1.61 | 2.45 | 0.15 | 0.13 | 25.18 | 2.79 | 1.01 | 0.81 | 25.92 | 0.70 |
| 33 | 1.61 | 1.54 | 7.08 | 0.18 | 0.34 | 0.27 | 4.80 | 3.40 | 0.17 | 0.15 | 27.95 | 0.98 | 1.36 | 1.08 | 19.80 | 1.18 |
| 26 | 1.63 | 1.56 | 7.40 | 0.23 | 0.30 | 0.25 | 3.57 | 2.77 | 0.21 | 0.18 | 30.71 | 2.40 | 1.38 | 1.04 | 27.73 | 1.30 |
| 25 | 1.65 | 1.58 | 7.49 | 0.22 | 0.26 | 0.22 | 3.28 | 1.57 | 0.17 | 0.16 | 23.50 | 4.94 | 1.05 | 0.89 | 13.48 | 1.44 |
| 174 | 1.67 | 1.60 | 7.73 | 0.22 | 0.30 | 0.27 | 4.16 | 2.37 | 0.20 | 0.18 | 25.84 | 2.82 | 1.32 | 0.86 | 44.60 | 0.90 |
| 1 | 1.70 | 1.62 | 7.98 | 0.22 | 0.48 | 0.41 | 0.29 | 5.20 | 0.23 | 0.20 | 27.30 | 2.42 | 1.51 | 0.81 | 70.08 | 13.70 |
| 187 | 1.75 | 1.67 | 8.41 | 0.21 | 1.01 | 0.88 | 4.52 | 0.54 | 0.25 | 0.22 | 26.68 | 1.91 | 2.04 | 1.14 | 63.05 | 0.06 |
| 188 | 1.80 | 1.71 | 8.85 | 0.37 | 0.63 | 0.59 | 5.03 | 6.99 | 0.10 | 0.08 | 34.24 | 6.73 | 2.17 | 1.07 | 33.52 | 9.03 |
| 189 | 1.86 | 1.77 | 9.45 | 0.72 | 1.54 | 1.42 | 2.98 | 1.25 | 0.76 | 0.53 | 30.56 | 29.77 | 1.99 | 1.03 | 30.19 | 6.73 |
| 190 | 1.92 | 1.82 | 10.07 | 0.50 | 0.75 | 0.71 | 0.64 | 1.02 | 0.49 | 0.46 | 39.83 | 21.75 | 1.59 | 1.00 | 47.68 | 6.52 |
| 191 | 1.98 | 1.87 | 10.64 | 0.41 | 1.20 | 1.18 | 0.33 | 0.23 | 0.47 | 0.42 | 37.31 | 10.72 | 1.72 | 1.04 | 45.94 | 0.27 |
| 192 | 2.04 | 1.92 | 11.08 | 0.44 | 1.00 | 1.00 | 0.00 | 0 | 0.49 | 0.42 | 35.82 | 6.85 | 1.57 | 0.92 | 29.69 | 2.93 |

*FIG. 25*

MICROFLUIDIC CHIP HAVING INTEGRATED ELECTRODES

This application claims benefit to U.S. Provisional Application No. 60/233,838, filed Sep. 19, 2000 and entitled "Integrated Microdevices for Conducting Chemical Operations" incorporated herein by reference in its entirety.

TECHNICAL FIELD

This invention relates to microfluidic chips and in particular, to microfluidic chips having integrated electrodes.

BACKGROUND

Miniaturized devices for conducting chemical and biochemical operations have gained widespread acceptance as a new standard for analytical and research purposes. Provided in a variety of sizes, shapes, and configurations, the efficiency of these devices has validated their use in numerous applications. For example, microfluidic lab chips are utilized as tools for conducting capillary electrophoresis and other chemical and biochemical analysis in a reproducible and effective manner. Microarrays or Bio-chips are used to conduct hybridization assays for sequencing and other nucleic acid analysis.

In a typical labchip, materials are electrokinetically driven through interconnected microchannels. Electrodes are positioned in reservoirs fluidly connected to the microchannels to make electrical contact with a medium contained therein. Application of a voltage across two electrodes will drive material from one reservoir to another based on electrokinetic transport phenomena. In a microfluidic device having numerous channels and reservoirs to perform multiplexed procedures, an electrode array (e.g., 10 to 100 or more electrodes) may be positioned such that each electrode makes electrical contact with the medium in the device. Programmable controllers may be electrically connected to the electrodes to individually drive the electrodes in a controlled manner. Examples of the use of voltages and electrodes to transport materials electrokinetically are disclosed in, for example, U.S. Pat. Nos. 5,126,022; 5,750,015; 5,858,187; 6,010,607; and 6,033,546.

Various problems arise, however, when electrodes are "dropped in" reservoirs on a chip. First, the electrodes are subject to contamination from previous testing. An electrode dropped into one test chip may introduce unwanted material into a device subsequently tested, thereby contaminating the subsequently tested chip.

Additionally, when conventional metal electrodes (i.e. platinum, gold, etc.) are used to apply electrical fields within certain conductive media such as aqueous conductive media, bubbles are prone to form thereby disrupting the intended operation of the device. This problem is exacerbated in applications such as capillary electrophoresis where higher voltages are desirable to achieve more efficient separations (i.e. higher throughput, better resolution, etc.).

Within an electrophoretic channel or in a reservoir connected thereto, gas bubbles (e.g., an air bubble) can interfere with the electrical connection or otherwise change electrical properties between driving electrodes and the conductive medium. When bubbles are formed, electrokinetic operations can be severely or completely inhibited. Accordingly, current protocols for conducting capillary electrophoresis utilize remedial electrode configurations and are limited to voltages that will not generate substantial bubbles. These conventional protocols, however, typically do not achieve the desirable higher throughput of systems employing relatively higher voltages.

"Dropped in" electrodes must also be carefully aligned and the depth must be controlled. Positioning the electrodes too deep may break the electrode or damage the device; positioning the electrode too shallow may prevent application of a voltage to the medium in the device and thus prevent driving the sample material through the device. Further, moving electrodes into position adds complexity to the instrument used to carry out the testing.

It is therefore desirable to provide a microfluidic device that does interfere with the intended operations of the microdevice yet can still be integrated with electrically conductive components necessary for chemical and biochemical operations, e.g., heating elements, electrodes, electrochemical detectors, valves, flow detectors and the like.

SUMMARY OF THE INVENTION

In one variation of the present invention, a microfluidic chip includes a substrate having interconnected microchannels and at least one aperture. A cover is bonded to the substrate to enclose the microchannels and form a reservoir at the at least one aperture. An electrically conducting ink is patterned on the cover or the substrate such that the electrically conducting ink makes an electrical connection with a medium contained in the microchannels or reservoirs. In a variation, an ink trace is positioned in the reservoirs and can be used to drive materials through the channels by application of a voltage to the ink trace. In another variation, the ink trace is positioned in a channel and is used to heat or detect materials in the channels.

In another variation of the present invention, a method is provided for reducing bubble formation during electrokinetic applications in a microfluidic device having channels and reservoirs. The method includes applying voltage to a medium contained in the channel and reservoirs through an electrically conducting ink. In one variation the electrically conducting ink is a trace patterned on a cover or substrate of the microfluidic device. In another variation, the electrically conducting ink is a coating on an electrode dropped in a reservoir in the device. A platinum wire electrode, for example, may be coated with an electrically conducting ink to reduce bubble formation in this variation.

BRIEF DESCRIPTION OF THE DRAWINGS

FIG. 4A shows the unassembled device. FIG. 4B shows the fully assembled device.

FIG. 25 is a summary chart for the field strength test (600 V/cm) using Ag/AgCl-ink-integrated microfluidic devices.

DETAILED DESCRIPTION

The present invention is directed to an integrated microdevice for conducting chemical operations. By chemical operations, it is meant analytical and research applications that are by nature, chemical, biochemical, electrochemical, biological, and the like.

In one variation of the present invention, a microfluidic chip includes a substrate having interconnected microchannels and at least one aperture. A cover is bonded to the substrate to enclose the microchannels and form a reservoir at the at least one aperture. An electrically conducting ink is patterned on the cover or the substrate such that the electrically conducting ink makes an electrical connection with a medium contained in the microchannels or reservoirs. In other cases, the ink electrode traces are not in direct connection with the medium. In a variation, an ink trace is positioned in the reservoirs and can be used to drive materials through the channels by application of a voltage to the ink trace. In another variation, the ink trace is positioned in a channel and is used to heat or detect materials in the channels.

In another variation of the present invention, a method is provided for reducing bubble formation during electrokinetic applications in a microfluidic device having channels and reservoirs. The method includes applying voltage to a medium contained in channels and reservoirs through an electrically conducting ink. In one variation the electrically conducting ink is a trace patterned on a cover or substrate of the microfluidic device. In another variation, the electrically conducting ink is a coating on an electrode dropped in a reservoir in the device. A platinum wire electrode, for example, may be coated with an electrically conducting ink to reduce bubble formation in this variation.

In yet another variation of the present invention the device employs one or more functional components adhered to a microfluidic device. Functional components, microchannels, microarrays, reservoirs, and apertures (through-holes) may be formed in the substrate or cover or the features may be formed in both the substrate and the cover. The parts may then be bonded together to form the microfluidic device of the present invention. Depending upon the application, by functional components it is intended electrically conductive elements that facilitate or enable the intended chemical operations. For example, functional components can be electrodes for manipulating charged entities, heaters, electrochemical detectors, valves, sensors for temperature, pH, fluid flow, and the like.

Other variations of the above described invention are disclosed hereinafter and other variations will become apparent upon reading the following description in conjunction with the accompanying drawings.

Microfluidic Devices

Figure 1:
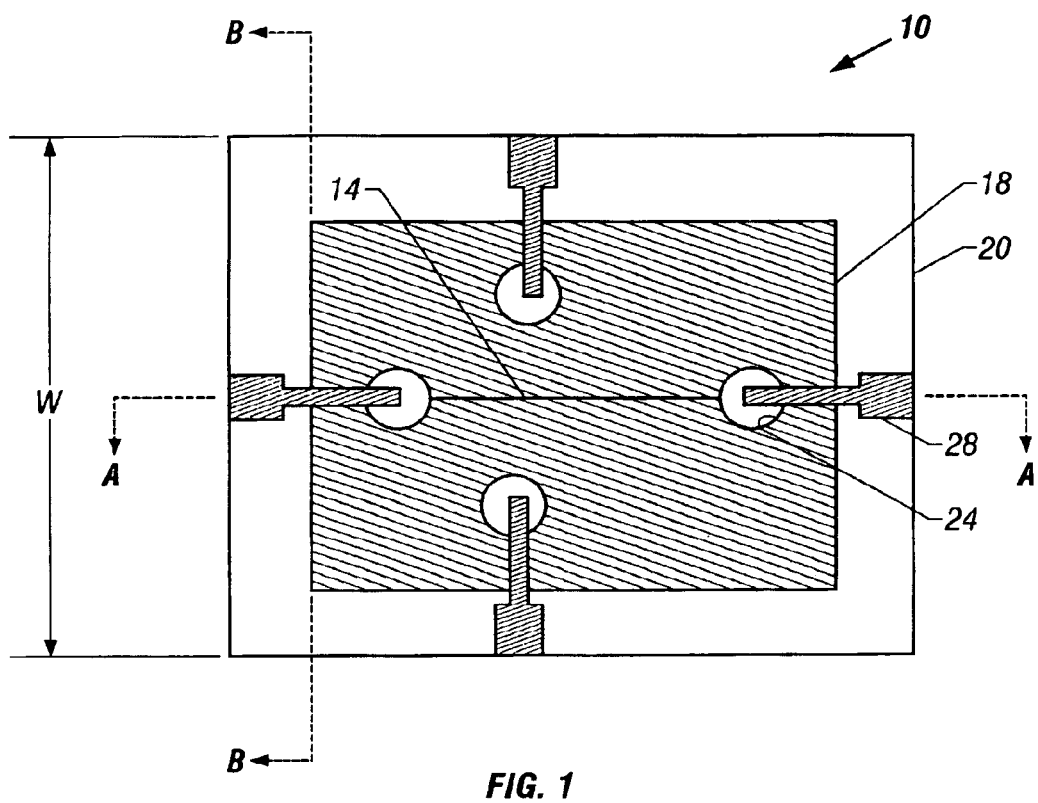
FIG. 1 shows a top view of a microfluidic device having integrated electrodes in accordance with the present invention.
Figure 2:
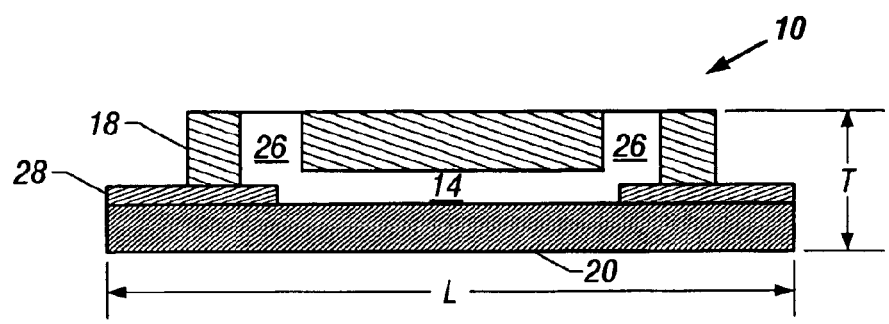
FIG. 2 shows a cross sectional view of the device shown in FIG. 1 taken along A—A.

An example of a microfluidic device or chip 10 in accordance with the present invention is shown in FIGS. 1 and 2. FIG. 1 is a top view of a chip 10 and FIG. 2 is a cross sectional view of the chip 10 of FIG. 1 taken along A—A. The microfluidic device 10 shown in FIGS. 1 and 2 is not to scale and is intended to illustrate structure which may be difficult to recognize if drawn to scale. In particular, the size of microchannel 14 relative to the thickness of the device 10 is exaggerated in FIG. 2.

Microfluidic device 10 includes a substrate 18 and a cover or plate 20 bonded to the substrate. While the substrate 18 is shown in the figures as a rectangular plate, the substrate may take a variety of different shapes including disc-like or other shapes. Further, the substrate is not limited to being positioned on top but may be positioned on the bottom of the microfluidic device or positioned in the microfluidic device between two components as in a sandwich configuration. Examples of microfluidic structures are described in, for example, U.S. Pat. Nos. 5,750,015, 5,126,022 and 6,033,546.

A substrate or chip preferably has a thickness (T), width (W), and length (L) of 0.005 to 0.5 inches, 0.5 to 10 inches and 1 to 10 inches, respectively. Additionally, certain films may be used as chips and be as thin as 0.005 inches.

The substrate 18 typically features at least one generally planar surface having one or more microchannels 14 and one or more apertures or through-holes 24 in fluid communication with the microchannels. Wells or reservoirs 26 are formed at the through-holes 24 when the cover 20 is bonded to the substrate 18 as shown in FIGS. 1 and 2. In one variation, a thin film cover is bonded to the bottom of the substrate thereby enclosing and sealing the microchannels. Access to the channels is provided via the through-holes in the substrate.

In a preferred embodiment, the subject integrated device can be configured as a microfluidic lab chip comprising channels generally having microscale cross-sectional inner dimensions such that the independent dimensions are greater than about 1 $\mu$m and less than about 1000 $\mu$m. These independent cross sectional dimensions, i.e. width, depth or diameter depending on the particular nature of the channel, generally range from about 1 to 200 $\mu$m, usually from about 10 to 150 $\mu$m, more usually from about 20 to 100 $\mu$m with the total inner cross sectional area ranging from about 100 to 40,000 $\mu m^2$, usually from about 200 to 25,000 $\mu m^2$. The inner cross sectional shape of the channel may vary greatly. Configurations include but are not limited to rectangular, square, rhombic, triangular or V-shaped, D-shaped, U-shaped, circular, semicircular, ellipsoid and the like.

Other suitable channel cross sections may be employed in the devices of the present invention. It is also preferred that channels have a surface finish that does not result in irregular flow effects or electric fields. The number of channels in communication with a given waste well may vary greatly. For example, only one channel may be so-connected. Alternately, upwards of 20 to 100 channels may empty into a single waste well. Further, it is contemplated that a number of interconnected channel functional units may be provided on a single chip. An example of a single channel functional unit is shown in FIG. 1.

While not shown, the cover may also include one or more microchannels and apertures. The cover may be a more or less rigid plate, or it may be a film. The thickness of the cover may be different for materials having different mechanical properties. Usually the cover ranges in thickness from at least about 200 $\mu$m., more usually at least about 500 $\mu$m., to as thick as usually about 5 mm or thicker, more usually about 2 mm. However, when the cover is a film, its thickness may be as small as 25 $\mu$m.

The cover and substrate may be molded in accordance with methods disclosed in copending provisional U.S. application Ser. No. 60/304,464 entitled "Injection Molding Techniques For Forming A Microfluidic Structure Having At Least One Flash Free Aperture" and filed Jul. 11, 2001. Further, the cover may be fabricated from a single material or a composite material. Suitable materials for the cover and substrate include but are not limited to glass, silica, ceramics, silicon, and polymers such as acrylics, polycarbonate, polystyrenes, noncyclic and polycyclic olefins such as polynorbornenes, and other polymers which are suitable for molding or forming. The cover may also be printed circuit board.

Preferably, the substrate material is amorphous, water insoluble, non-porous, nonpolar (electrically neutral) and electrically non-conductive, i.e. has a high electrical resistance. Preferably, the material is stable having sufficient mechanical strength and rigidity to retain its shape under the conditions required for chemical operations. For instance, capillary electrophoresis often requires the use of a salt containing aqueous media in which the pH may range from 2 to 12. Useful polymers are preferably thermoplastic and suitable for precision forming or shaping using conventional molding and extrusion processes. Web based film processing is also possible where the subject polymer is extruded into a substrate form. See, for example, PCT/US98/21869. Useful polymer films prepared will generally have a thickness in the range of about 25 $\mu$m to 1000 $\mu$m, more usually in the range of about 25 $\mu$m to about 750 $\mu$m.

Preferably, the substrate material can also withstand the required exposure to chemicals and heat required for curing or patterning integrated electrodes. For instance, binders in conductive inks that exhibit high glass transition temperatures require the use of elevated temperatures during bonding or curing.

Integrated Electrodes

Referring again to FIGS. 1–2. microfluidic chip 10 also features integrated electrodes 28. Integrating electrodes into chip 10 eliminates the need to "drop in" electrodes as described above. Each electrode 28 is shown positioned in the reservoirs 26 such that the electrode electrically contacts a material or medium contained in the reservoir. Suitable materials and mediums include but are not limited to fluids (e.g, buffered solution, electrolyte solutions) and gels such as polyacrylamide gel and agarose. Suitable materials also include samples comprising one or more charged entities.

The electrodes 28 may be connected to a programmable voltage controller for applying desired voltage differentials across the channels. In operation, samples may be added to one or more of the reservoirs and are electrokinetically driven through the microchannels to carry out various biochemical processes such as those mentioned above. Types of microfluidic applications and voltage control for manipulating materials in the various channels are described in a number of patents including, for example, U.S. Pat. Nos. 5,126,022; 5,750,015; 5,858,187; 6,010,607; and 6,033,546.

In addition to being used as driving electrodes, the integrated electrodes may be used for other functions including: heating elements, electrodes, electrochemical detectors, sensors for pH, temperature, fluid flow, pressure and the like. In this manner, the electrodes are functional components which can be used to induce and control movement of fluids through the application of an electrical potential or current, control temperatures within localized areas of the device, enable electrochemical detection, control hybridization or binding of entities, conduct mixing of fluids, monitor flow, and the like. For determination of specific design and composition, it should be understood by those skilled in the art that the components must be electrically conductive. By electrically conductive, it is meant that these components are capable of conducting more than trivial amounts of electricity. The electrical resistance may be high or low, depending on many factors including electrical properties of the component's composition as well as its dimensions. For ordinary electrical conductors, low resistance is generally preferred. For resistors, higher resistances are usually desired. The resistance should not be so high, however, that for practical purposes they are not significantly conductive, as would be understood by those skilled in the art. From conventional equations 1 and 2, below, it is readily apparent that the design parameters of the components, i.e. width, shape, composition and thickness, are dependent upon desired resistance and conductivity.

$$V = IR \qquad \text{Equation 1:}$$

where V is applied potential, I is the generated current, and R is overall resistance.

$$R = \rho * L/A \qquad \text{Equation 2:}$$

where R is overall resistance, $\rho$ is resistivity of the conductive material, L is the length of the component and A is its cross sectional area.

Accordingly, the relative dimensions of the components will be determined by their intended function, i.e. a component that generates heat will generally have a higher resistance and a component that provides a voltage gradient from a specific power supply will usually have a lower resistance.

Conveniently, the subject components will be provided as a film or layer adhered or strongly adhered to the surface of the substrate. The thickness of this film will generally be in the range of about 50 Å–4000 Å, more usually about 1500 Å to 3500 Å, usually about 2000 Å–3000 Å. For some integrated components such as integrated ink electrodes, the thickness may range from 5 to 100 $\mu$m and more usually from 10 to 20 $\mu$m. The width of the film will be optimized according to relative design limitations. For instance, the greater the width of the component, the more susceptible it is to delamination. On the other hand, a narrower film inherently generates a higher resistance. Accordingly, the width of the subject components will usually be in the general range of about 1 $\mu$tm to 1000 $\mu$m. For some integrated component such as integrated ink electrodes, the width may range from 50 to 4000 $\mu$m and more usually from 100 to 1000 $\mu$m. The length of the component is similarly determined by various design factors such as the required absence or presence of heat, the required voltages or currents, and the composition of the components.

Electrically conductive components preferably are able to withstand exposure to relevant chemical reagents or samples, for example, where the component is a sensor for pH measurements or electrochemical detection.

Electrically Conducting Inks

In one variation, the electrically conducting components or electrodes are an electrically conducting ink. However, other conducting materials are suitable given they do not deter from assembling the components as discussed further below. Examples of suitable inks for use as electrodes in accordance with the present invention include polyester or acrylic-based carbon/graphite ink, platinum ink, silver ink, silver/silver chloride ink, and metal powder doped carbon ink. However, other inks containing conductive metals or graphite may be used in the present invention. Such inks are well known in the art. See, for example, U.S. Pat. No. 5,047,283 and its cited references for a general description of electrically conductive inks printed on polymer surfaces, each of which is incorporated herein by reference. In yet another embodiment, the electrodes or functional components can consist of an epoxy resin comprising an electrically conductive portion, usually metal.

Use of ink components or ink patterns is desirable because bubble formation is reduced during application of voltages to a medium in electrophoretic applications. Bubbles are usually generated on conventional electrodes (e.g., platinum or gold electrodes) during electrophoresis and can terminate the experiments or affect the separation results, especially for longer separation experiments, like DNA sequencing. However, bubbles on carbon ink electrodes are rarely observed in assay experiments. This bubble reduction phenomena may be because of the unique electrode morphology (higher surface area and porous surface). In the case of Ag/AgCl ink, no bubbles were observed during electrophoresis because of the Reduction of $Ag^+$ or the oxidation of Ag in the ink. In any case, it enables the application of higher voltages or electrical fields in electrokinetic applications thereby resulting in more efficient operations. Relative to capillary electrophoresis, this translates into more efficient separations and higher resolving capability.

Further, during longer DNA separations where bubbles are more likely to form, the electrodes may be positioned or deposited on the device such that the chip performance is not affected. By placing electrodes in the reservoirs or wells distal to the channel as shown in FIG. 1, bubbles formed in the reservoir are prevented from entering into the channel and thus separation performance in a controlled mode can be achieved.

Importantly, different inks can be selected based on specific applications. For example, Pd-doped carbon ink electrodes can be used to reduce the bubble generation on cathode because of the formation of the Pd hydride. Ag/AgCl ink can be used, for example, to totally suppress the bubble generation during electrophoretic separations at both the cathode and anode. This follows from the following equations:

Anode: $Ag-e^-=Ag^+$

Cathode: $AgCl+e^-=Ag+Cl^-$

The electrochemical results, discussed infra, support the above statements regarding bubble suppression. Ink itself can be used as a matrix (or support) for incorporating other agents to eliminate bubble generation.

Accordingly, the present invention includes use of inks not only to drive, heat, detect and control materials in electrokinetic applications, but also to suppress and reduce bubble formation. As noted above, bubble reduction and suppression may be carried out by simply applying an ink pattern for use as an electrode itself or by coating a wire or other type of electrode with an electrically conducting ink.

The above discussed electrically conducting ink and electrode patterns preferably incorporate conductive leads. In other words, the ink and electrode patterns preferably include a functional portion or component and other features such as leads, contact regions, and any other useful feature in carrying out the invention.

Incorporating leads into the electrode pattern enables the delivery of a power source to the component as in the cases of heaters or electrodes for driving charged entities, and the delivery of a signal from the component to relevant monitoring equipment, such as in the case of a sensor for monitoring pH, electrochemistry, temperature, flow, and the like. These leads are subject to the same design parameters and limitations to the functional components as referenced above. Preferably, thin film connections are utilized from the edge of the chip. This facilitates electrical connection of the device with automated electronics, for example a computer processor for operating the device, i.e. administering current, monitoring conditions within the device, and the like. An example of such a lead connection in a microfluidic device is described in U.S. Pat. No. 5,906,723 which is incorporated herein by reference. Another benefit of using a thin film connection readily becomes apparent with the manufacture of a multi-layered device where leads to the component that are interposed between two layers can interfere with the bonding or sealing of a laminate device.

In one embodiment, the leads to the functional components can consist of wires directly connected to the device. By directly connected it is intended that the leads are in contact with the components such that an electrical current can adequately pass through the connection. Preferably such a connection is accomplished through soldering or other known methods for keeping two conductive surfaces in contact with each other. In another embodiment, such as that illustrated in FIG. 9, the lead(s) 100 can be integral to the component 101 itself comprised of a single film patterned into relevant functional regions.

Figure 4A:
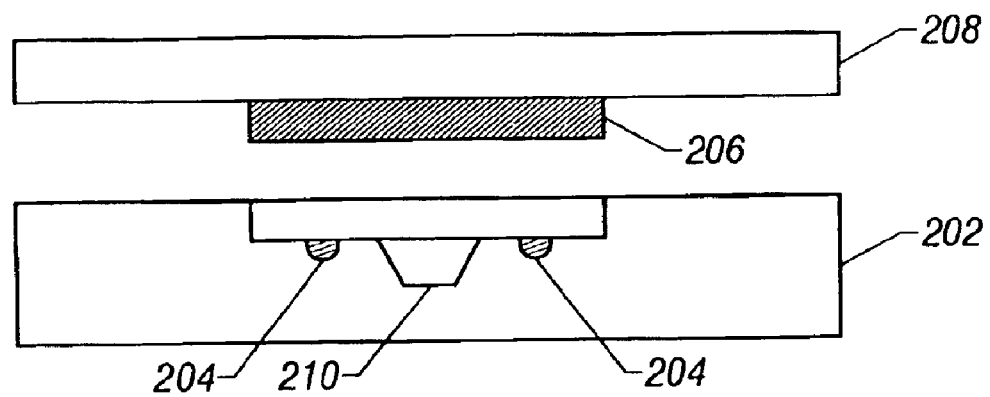
FIGS. 4A and 4B show a cross sectional view of a microfluidic device having two microchannel systems: one system providing the leads to an electrode and the other system providing for an analytical capillary channel.
Figure 4B:
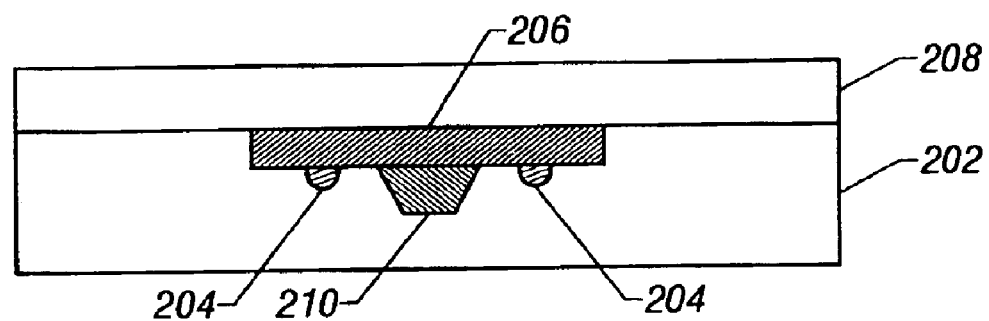

In another embodiment, the leads can be comprised of an electrically conductive fluid. Depending upon the application, such a fluid can be electrically conductive, thermally conductive or both thermally and electrically conductive. With reference to FIGS. 4A and 4B, electrical connection to the functional component can be accomplished through the use of microchannel networks 204 filled with the conductive fluid and in fluid connection with the component 206. The dimensions of the microchannels are in accordance with the required design parameters of the leads. One variation on this approach would be that in which the electrically conductive fluid comprises the functional component itself, for instance, a serpentine channel that is filled with an electrically conductive fluid is an example of a working design for a heater element. Another variation would be to introduce a conductive fluid into the microchannels which will subsequently cure into a solid form that is stable and integral to the device. In the alternative, localized regions of the fluid can be selectively cured, i.e. photocurable fluids selectively exposed to UV light. Such designs may be particularly useful for the manufacturing of the provided devices, especially those that may be multidimensional or multi level. Curable conductive fluids would include epoxy resins and inks comprising an electrically conductive portion, usually metal or graphite. Other examples of electrically conductive fluids include uncured inks and ionic or electronic liquid conductors. For example, aqueous salt solutions and liquid metals are useful in the invention. Conveniently, liquid metals such as mercury can be used in order to avoid hydrolysis and the generation of gases from reduction and oxidation processes present at electrodes where ionic solutions are utilized. Such reactions can also be minimized through the use of ionic entities in nonaqueous solvent such a methanol and the like.

Other approaches include tailoring the components and the conductive fluid, for example, coating electrodes with silver chloride in combination with the use of an aqueous solution of chloride ions as the conductive fluid. In one variation, as discussed above, platinum electrodes are coated with a conductive ink to reduce air bubble formation. The inks may be the same as those mentioned above and have a thickness of 5 to 500 $\mu$m. and more preferably between about 10 and 150 $\mu$m.

In the cases where electrically conductive inks are the provided embodiment, the inks can be applied to the substrate through a variety of printing approaches including but not limited to screen printing, ink jet applications, printing presses, pad printing and the like. Similarly, the ink can also be patterned through conventional lithography where needed. The adhesion of ink on certain substrates such as polycyclic olefin is weak. However, plasma or corona treatment may be used to treat the surface of the substrate to improve adhesion.

The present invention thus includes various methods of applying ink electrodes to a substrate. The present invention also includes but is not limited to the use of certain substrates which have characteristics uniquely suited for various processing conditions. For example, the subject substrates may be chosen to be uniquely suited to an application in that they are highly resistant to processing conditions required for ink application. For a general description of printing electrically conductive inks on polymer surfaces, see U.S. Pat. No. 5,047,283 and its cited references, each of which is incorporated herein by reference.

Accordingly, a heat-resistant substrate may be preferred in certain situations. For example, in high throughout production lines, ink may be applied in a continuous manner onto a thin plastic film supplied by a reel. The coated film may then be moved through a heat tunnel to facilitate curing of the ink. For fast curing, the temperature must be relatively high to ensure the ink will cure before the next step in the fabrication process.

The present invention also includes use of polymers sensitive to processing conditions such as polymers with ordinary or low resistance to temperature. When using such polymers, however, more time must be allotted for curing. Curing could be carried out individually or in batch processes wherein the ink is simply allowed to cure over time at room temperature or a temperature which does not damage the polymer.

In sum, the present invention includes patterning ink onto substrates made of various materials. The materials used to form the substrate and cover may vary greatly. Preferably, the substrate material possesses an overall combination of properties that makes it optimally suited for relevant processing and operation. A preferred substrate, for example, is a norbornene based substrate.

Bonding Techniques

Figure 3A:
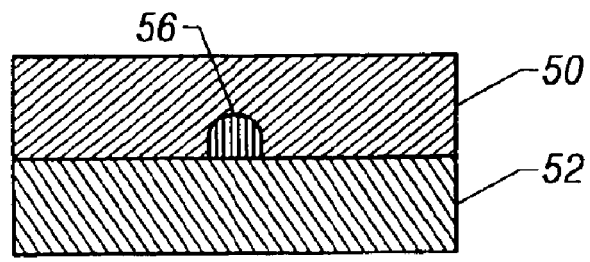
FIGS. 3A–3B show cross sectional views of the device shown in FIG. 1 taken along B—B having various assemblies in accordance with the present invention.
Figure 3B:
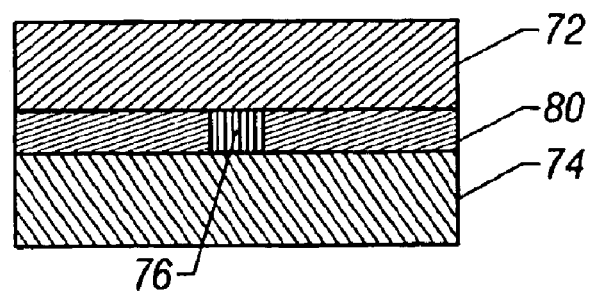
Figure 3C:
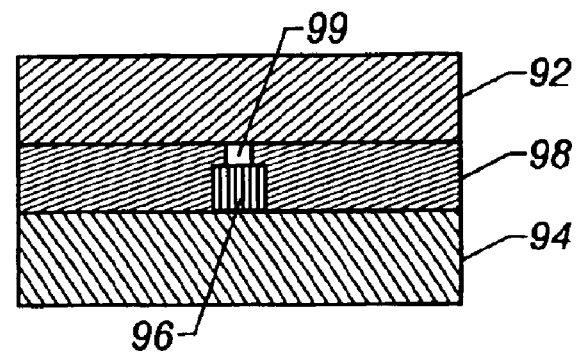
FIG. 3C shows a cross-section of a variation of the present invention wherein a channel is formed due to an adhesion layer overlapping the electrodes.

The present invention also includes novel bonding techniques. FIGS. 3A–3C depict bonding techniques in accordance with the present invention. In particular, FIGS. 3A to 3B are cross sectional views of the device shown in FIG. 1 taken along B—B. Note that FIGS. 3A to 3B are not drawn to scale and are intended to show structure which would be difficult to see if drawn to scale.

A preferred assembly is illustrated in FIG. 3A. Referring to FIG. 3A, a substrate 50 is thermally formed around electrode 56. Surprisingly, a fluid tight seal can be formed along the electrode traces despite the presence of the electrode traces between the substrate and the cover. The device 50 thus features fluid tight sealing of microchannels, reservoirs and integrated electrodes. An exemplary construction includes a screen printed conductive ink electrode trace on a cover 52 such as a thin film of plastic. The thin film of plastic is thermally laminated to a substrate having microchannels, wells and other useful features in carrying out microfluidic applications. Importantly, we have found that this exemplary configuration does not leak along the electrode traces when fluids are added to the reservoirs.

Another suitable assembly is illustrated in FIG. 3B. Referring to FIG. 3B, a device 70 includes a substrate 72, a cover 74, an electrode 76, and an adhesive layer 80 disposed between the cover and the substrate to bond the components together and form a fluid tight seal at the interface where the substrate and cover contact the electrode. The adhesive 80 may be a pressure sensitive adhesive (PSA). The adhesive 80 is preferably applied, printed or patterned on the cover around the electrode 76 and along the edges of the channels and reservoirs; the adhesive may simply be applied around the electrode 76 to the rest of the cover. An exemplary construction includes screen printing a conductive ink electrode trace on a cover such as a plastic film. PSA is then screen printed on the cover around the ink electrode traces. The PSA coated cover is then pressed against a substrate containing channels and wells. Importantly, we have found that this exemplary configuration does not leak along the electrode traces when fluids are added to the wells and channels. Suitable PSAs include but are not limited to hot melt or solvent based PSA.

Another suitable assembly is illustrated in FIG. 3C. Referring to FIG. 3C, a device 90 includes a substrate 92, a cover 94, an electrode 96, and an adhesive layer 98 disposed between the cover and the substrate to bond the components together and form a fluid tight seal around the electrode. Unlike the configuration shown in FIG. 3B, the adhesive layer 98 in this configuration overlaps the electrode thereby forming a space or channel 99 in the device. The adhesive thus acts as a spacer as well as a seal.

The adhesive 98 is applied to the cover as discussed above and is preferably a double sided adhesive layer. The cover 94 is then laminated or pressed onto the substrate. An exemplary construction includes screen printing a conductive ink electrode trace on a plastic cover such as a plastic film. A double sided PSA is then laminated onto the cover. Suitable PSAs include but are not limited to 3M 1522. Next, a substrate having microchannels and wells is pressed against the adhesive layer to enclose the microfeatures and form a seal.

The integrated components or electrodes can be provided in a number of configurations. For instance, the microdevice can comprise a single layer or a laminate as in FIG. 4A where each layer can provide a functional aspect to the device. For example, one layer may serve as a first substrate 202 where the microchannels 210, 204 and other features, e.g. reservoirs, may be cut, embossed, molded, etc. The other layer(s) may be used as substrates 208 for incorporating the functional components, providing ports or wells, and for sealing the microchannels and other features of the first substrate.

As shown in FIG. 4B, the layers are brought together in an orientation such that the integrated components and various features on all the layers can interact accordingly with the microchannel. As stated above, joining the individual layers may be accomplished by heating, adhesives, thermal bonding, or other conventional means. Commonly, the devices are prepared by molding a substrate with the individual features and components present in the substrate and then applying a cover layer to enclose the microchannels, where access to the reservoirs may be provided in the molding process or by the cover layer. In a variation to this design, the components can be integrated in an independent cover lid that seals the reservoirs or sample wells of the device and minimizes evaporation. In such a configuration, the components will generally consist of driving electrodes positioned such that they will be in fluid contact with the reservoirs.

Applications

The present invention may be used for various applications. Placement of the components relative to the other microfeatures of the device may be tailored to optimize the desired application. For instance, where electrochemical detection is desired in an electrophoretic device, the positioning of the electrodes relative to a driving potential affect sensitivity and resolution.

Figure 5:
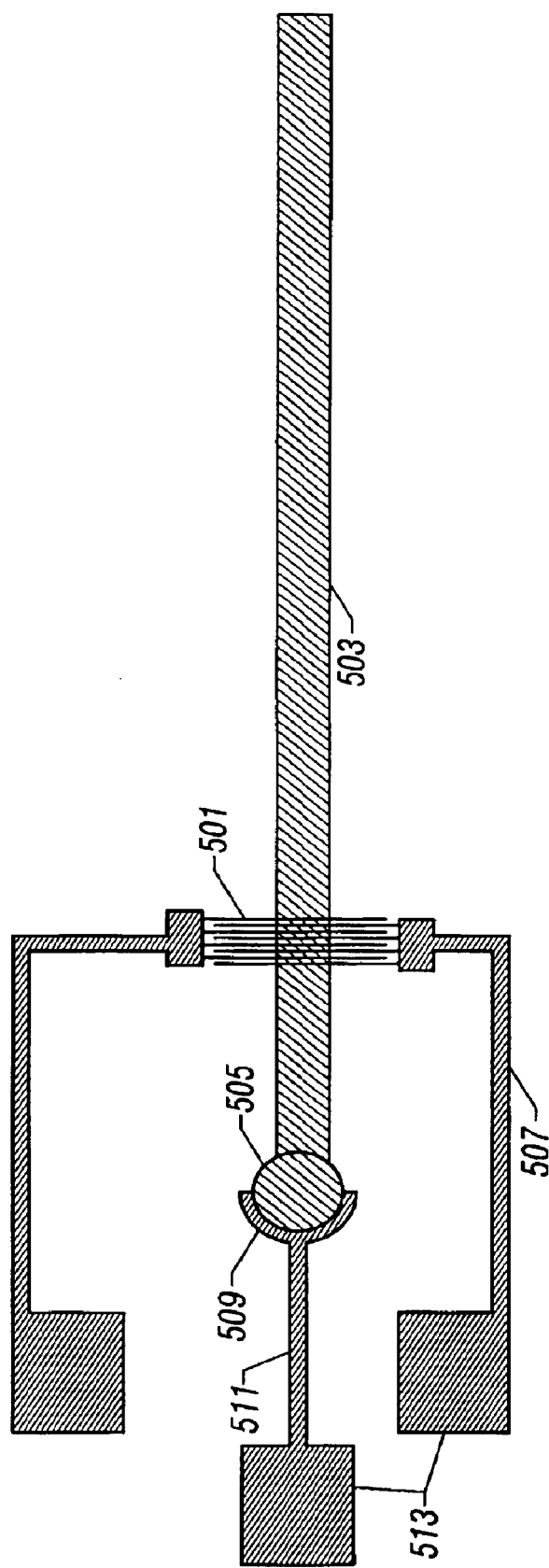
FIG. 5 shows a top view of a microanalysis channel in accordance with the present invention that has both an electrochemical detector and a semi-circular driving electrode integrated therein.

FIG. 5 shows one design for an electrochemical detector that demonstrates such a configuration. The detector is comprised of interdigitated detection elements 501, leads 507 and contacts 513. The detection elements 501 are located near the end of the capillary channel 503 for purposes of optimizing detection signals. For a general description of electrochemical detectors and their placement relative to electrophoretic channels, see U.S. Pat. No. 5,906,723 which is incorporated herein by reference. If the component is to serve as a driving electrode for controlling movement of fluids, the electrode should be placed in fluid connection with the channel 503, either directly or through a permeation layer, at opposite ends, alongside, or in localized regions of the channels. Preferably the electrode 509, connected through lead 511 to contact 513, is placed or positioned in a reservoir 505 located at the end of the channel 503. The driving electrode can be provided in a variety of shapes and dimensions, such as a half circle 509 or whole circle in fluid connection with the reservoir 505.

Figure 6A:
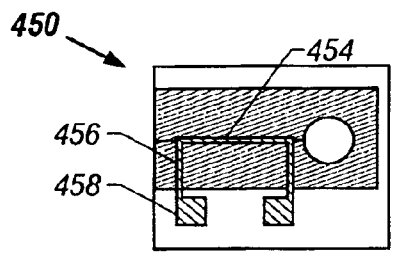
FIGS. 6A and 6B show a top view and cross sectional view of a microfluidic device having an integrated electrode heater in accordance with the present invention.
Figure 6B:
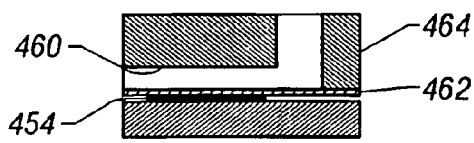

FIGS. 6A and 6B show another configuration of the present invention having integrated electrode heating elements. Referring to FIG. 6A, a partial top view of a device 450 is shown having an electrically conducting ink pattern incorporated therein. In particular, FIG. 6A depicts a heating element 454 as a single linear strip ink electrode. The ink pattern also includes leads 456 and contacts 458 to provide a convenient electrical connection to a voltage or current source. Current is applied to the heating element via contacts and leads to heat the channel 460. Also, the heating element 454 is not in direct contact with the channel and is separated by a cover 462. Cover 462 is shown bonded to substrate 464 thereby enclosing channels 460. The device 450 also may include a support. Notably, this configuration has been found to suitably heat materials in the channel 460. Further, the heat may be controlled by varying other properties or parameters of the device such as the voltage supplied to the electrode.

Figure 6C:
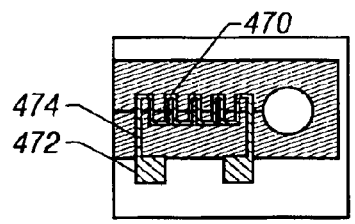
FIGS. 6C and 6D show a top view and cross sectional view of another variation of a microfluidic device having an integrated electrode heater in accordance with the present invention.
Figure 6D:
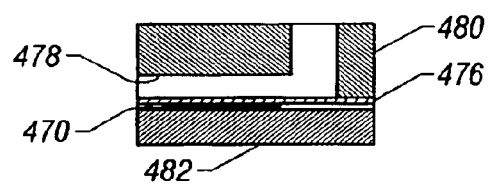

FIGS. 6C and 6D show another variation of the present invention comprising a heating element. In this configuration, electrically conducting ink heating element 470 is serpentine shaped and is shown having square-like turns. The pattern, however, need not be square-like and other patterns may be employed. The configuration shown in FIGS. 6C and 6D also include contacts 472 and leads 474. The heating element 470 is positioned below cover 476 and is not in fluid communication with channel 478. Cover 476 is shown bonded to substrate 480 thereby enclosing channel 478. Support 482 may also be included beneath heating element 470. Using this configuration, we have found that the measured resistance is higher than a straight strip and that materials in channel 478 may be heated when voltage is applied to the electrically conducting ink pattern 470.

Figure 7A:
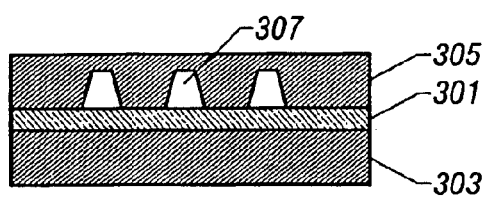
FIGS. 7A–7C show cross sectional views of an integrated device in accordance with the present invention having alternative configurations: in particular, the electrode (indicated by reference numeral 301) is shown in a different position relative to the other components in each of FIGS. 7A–7C.
Figure 7B:
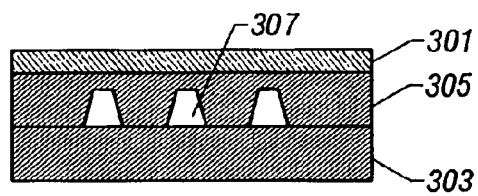
Figure 7C:
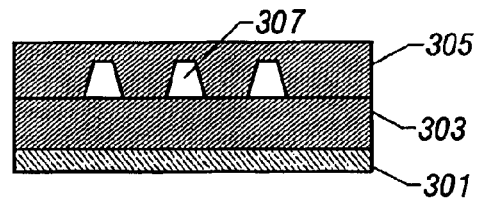

While the heating elements have been shown thus far as being positioned below the cover and not in fluid communication with the channel the invention is not so limited and other configurations may be employed. For example, a component 301 can be provided on a cover film 303 that seals the channels 307 as shown in FIG. 7A such that the component 301 is in direct contact with the channel contents; a component may be adhered to the opposite side of the channel substrate 305 as shown in FIG. 7B; and the component can be provided on the exterior surface of the cover film as shown in FIG. 7C. By component it is intended to include but not be limited to electrodes such as electrically conducting ink electrodes patterned on a cover or substrate.

Figure 8:
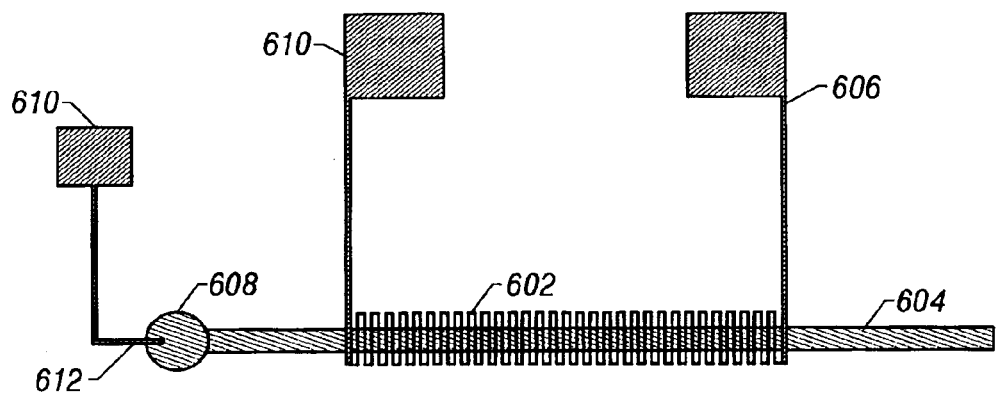
FIG. 8 shows a top view of a microanalysis channel in accordance with the present invention that has both a heater and a driving electrode integrated therein where the driving electrode has a minimized surface area for reducing unwanted hydrolysis or gas generating reactions.

Another configuration is shown in FIG. 8 where the driving electrode 612, located in reservoir 608, is merely an extension of the lead, whereby hydrolysis is minimized by the smaller surface area of the provided electrode. For purposes of controlling temperature, the components can be configured as heaters placed within certain localized regions along the channel of interest, e.g. 604. One design for such a heater includes a serpentine-like heater element 602, leads 606, and contacts for the power supply 610. Another heater design includes a heater element that is a solid band as described in FIG. 6A above and variations or combinations in between.

Figure 9:
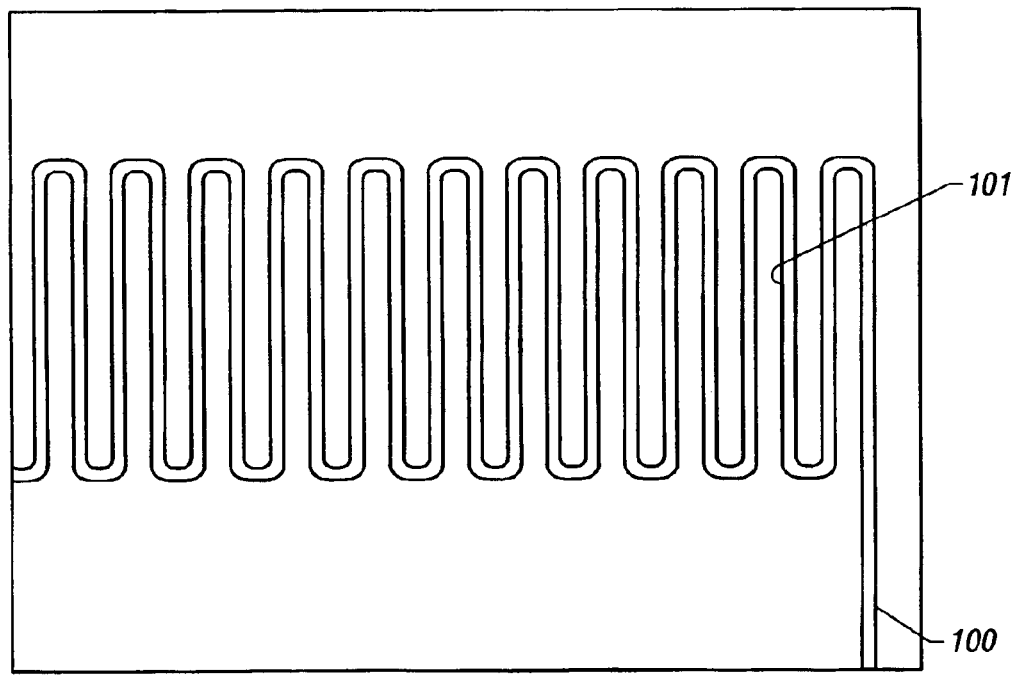
FIG. 9 shows a top view of a heater integrated into a norbornene based substrate. The pattern includes a metal heating element and its incorporated lead.

With reference to FIG. 9, heater 100 integrated on the surface of a norbornene based substrate is shown whereby the heating element portion 101 of the component is serpentine in shape and is of a length of about 230 mm. Its width is approximately 100 $\mu$m and its thickness is about 2000 Å. The heater is comprised of gold with a resistance of 790 $\Omega$ under an operating voltage of 25 V. The leads providing current to this heater are incorporated into the gold film, also having a thickness of about 2000 Å. Their width is also about 100 mm while their length is about 12 mm. The intended application of this particular heater design is to control the temperature in a microfluidic channel. Its general orientation is orthogonal to the particular length of a microchannel so as to heat the channel contents in a localized region of the device. Techniques for depositing metal films are described in U.S. Provisional Application 60/233,838 which, as mentioned above, is incorporated by reference in its entirety.

The invention may be directed to other applications. For monitoring flow, for example, electrodes are optimally positioned within the channel to ensure accuracy, i.e. downstream and immediately adjacent to the location of sample injection or around the detection zone. For general examples of microchannels, channel networks, microfluidic chips and their operation, see U.S. Pat. Nos. 5,750,015, 5,858,188, 5,599,432 and 5,942,443 and WO96/04547, each of which is incorporated herein by reference.

In another preferred embodiment of the claimed invention, the device can be configured as an electronic microarray device incorporating components for conducting hybridization assays. The components in this embodiment can comprise individually addressable sites for localizing reactions. For general examples of such devices, including structure and operation, see U.S. Pat. Nos. 5,605,662, 5861242, and 5,605,662, each of which is incorporated herein by reference.

EXAMPLES

Various microfluidic devices in accordance with the present invention were tested. The tests included: (1) on-chip electrophoretic separations using electrically conducting ink electrodes; (2) field strength tests using electrically conducting ink-integrated labcards; (3) electrophoretic separations using wire electrodes having an electrically conductive ink coating and (4) heating using integrated ink electrodes.

On-chip Electrophoretic Separations

A microfluidic device as depicted in FIGS. 1 and 2 was fabricated and tested. In particular, electrically conducting ink electrodes were used as driving electrodes for electrophoretic separations for different assays and DNA sequencing. The device included a poly(methyl methacrylate) (PMMA) substrate and PMMA thin film cover thermally bonded to the substrate. The channels formed in the substrate were about 50 $\mu$m. in depth. A 10 to 30 $\mu$m ink coating was applied to the cover using screen printing technology to form the ink pattern depicted in FIG. 1 before sealing.

Enzymatic assays were run in the above described devices. The enzymatic assay included P450 assay and kinase assay. The incubation can be done both off chip and on chip. The data shown in this patent are for off-chip incubation. For P450 assay, the substrate used is dihydrofluorescein diacetate, and the enzyme is CYP3A4. The enzyme reaction mixture contained 100 nM CYP3A4, 50 uM dihydrifluorescein diacetate, 2.12 mM NADPH, 40 mM HEPES pH 7.4, 30 mM $MgCl_2$, 2.4 mM reduced glutathione, and a certain concentration of a stop reagent. The enzyme reaction was initiated by adding NADPH to the reaction mixture after 3 min. incubation of CYP3A4 with its substrate at 37° C., and the reaction was stopped for analysis after 30 minute incubation. Carboxyfluorescein was added as an internal standard (125 nM). For kinase assay, 30 pg/ul Src kinase, 5 uM substrate (SBQX-4), 100 uM ATP, 50 mM HEPES pH 7.4, 20 mM $Mg(Ac)_2$ and a certain concentration of a stop reagent were in the enzyme assay mixture. The mixture was incubated at room temperature for 30 minutes. 100 nM fluorescein was added as an internal standard after the incubation.

Figure 10:
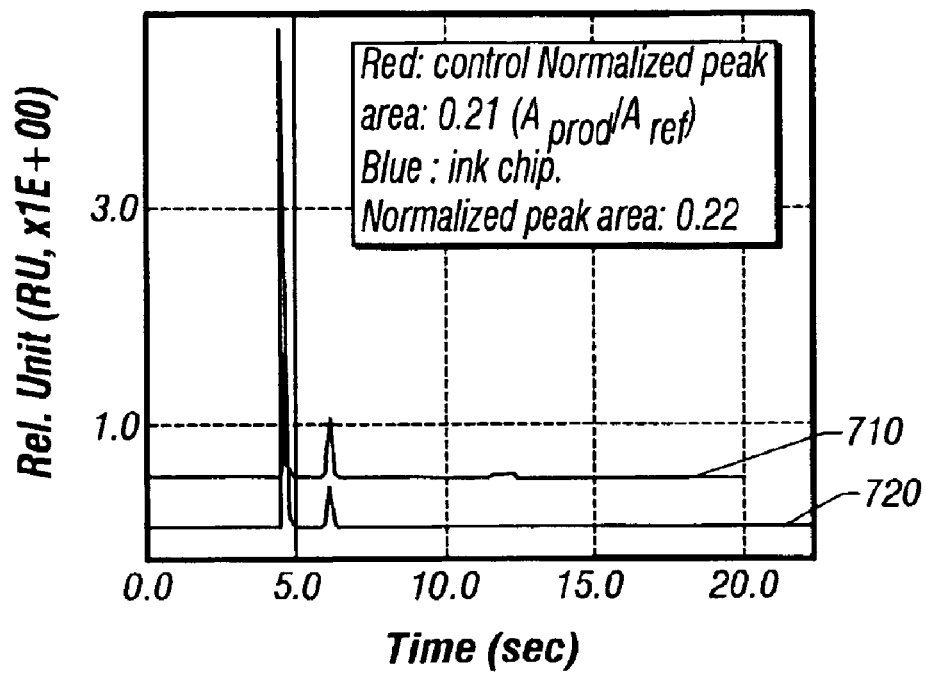
FIG. 10 shows an electrophoretic separation for P450 assay on conductive ink-integrated chip: the line at the bottom is the control experiment using platinum wire as electrodes and carboxyfluorescein is used the internal reference.
Figure 11:
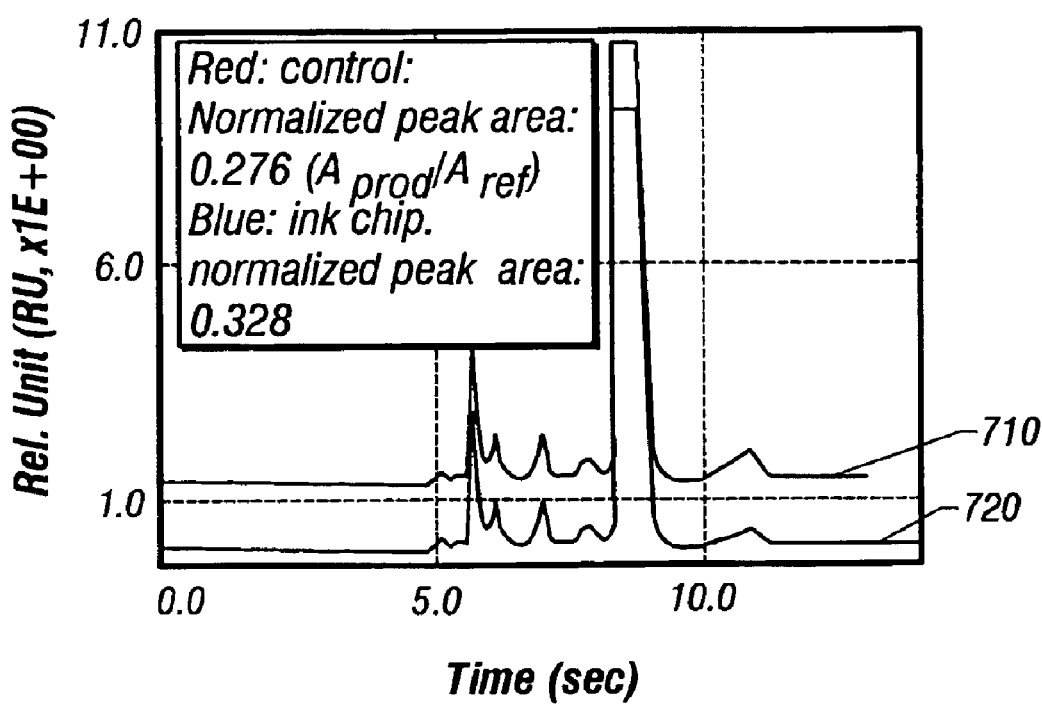
FIG. 11 shows en electrophoretic separation for Kinase assay on conductive ink-integrated chip in accordance with the present invention: the line at the bottom is the control experiment using platinum wire as electrodes and carboxyfluorescein is used as the internal reference.

FIGS. 10–11 show that the results of the enzymatic assays using integrated chips. The carbon electrodes can last at least 10 runs and give stable current and reproducible separation results. Reference numeral 710 represents the carbon ink electrodes. The results from control experiments where platinum wires were used as driving electrodes are also given in the figures for comparison. References numeral 720 represent the control. The results obtained using integrated electrodes are nearly identical to those obtained from external Pt wires. The current is very stable during sample injection and separation.

DNA separations were also run in the above described devices. The DNA separations included Genescan 700 with 18 fragments.

Figure 12A:
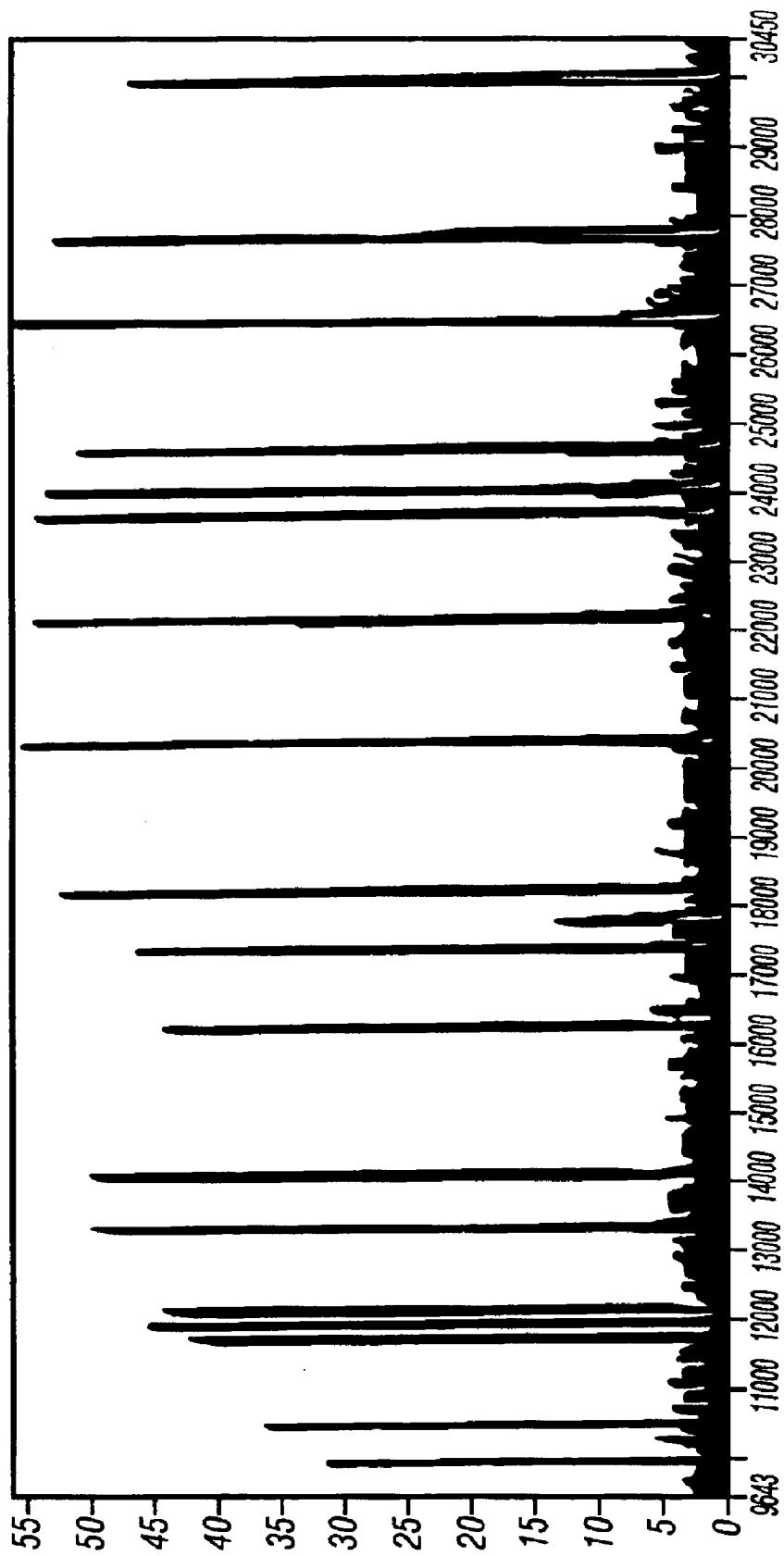
FIG. 12A shows DNA separation using ink-integrated microchips in accordance with the present invention: the sample is Genescan 700, denatured at 95° C. for 2 minutes and chilled down on ice and the 18 peaks are 75, 100, 139, 150, 160, 200, 250, 300, 340, 350, 400, 450, 490, 500, 550, 600, 650, and 700 base pairs DNA fragment.
Figure 12B:
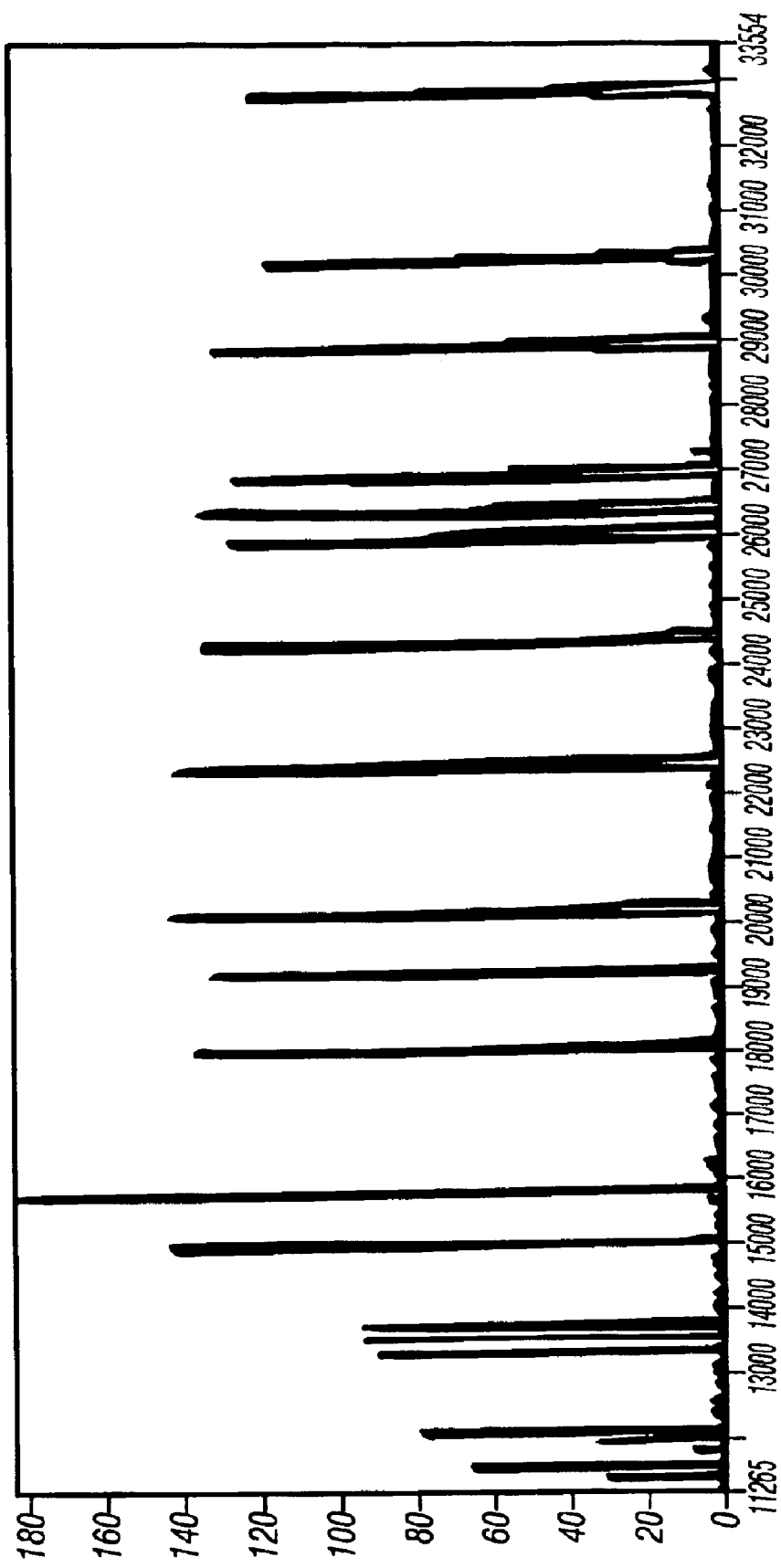
FIG. 12B shows DNA separation using platinum wires as driving electrodes (the control experiment): the sample was Genescan 700, denatured at 95° C. for 2 minutes and the 18 peaks are 75, 100, 139, 150, 160, 200, 250, 300, 340, 350, 400, 450, 490, 500, 550, 600, 650, and 700 bp DNA fragment.

For DNA separation, the ink-integrated DNA chip has a separation length of 18.5 cm and an offset of 250 μm. The dimension of the channel was 50 by 120 μm. This device gave all the expected 18 DNA fragments, as shown in FIG. 12A. The crossover plot shows separation of up to 385 base pairs DNA molecules on an acrylic chip at room temperature, better than the results using Pt wire as electrodes (340 bp, FIG. 12B). However, as evidenced in FIGS. 12A and 12B respectively, the signal from the chip using carbon ink as electrodes is about 30% of that from chip using Ft as electrodes. The carbon ink on plastic chip can survive at least 10 runs, each nm takes over 3000 s, suggesting that the printed carbon ink is very robust and reliable.

We also tested electrophoretic separations of four eTag™ probes in a device made in accordance with the present invention. eTag™ probes consist of a fluorescent moiety attached to a charged molecule having a characteristic electrophoretic mobility. Each probe is, in turn, attached to a nucleic acid sequence keyed to a desired RNA or DNA target. The probe sequence can be encoded by the electrophoretic mobility of the cleaved eTag™ probes, which are released (cleaved from the nucleic acid sequence) during a nuclease-catalyzed reaction. Therefore, reliable, high-quality separation is essential to enable the multiplexed expression assay.

Figure 13:
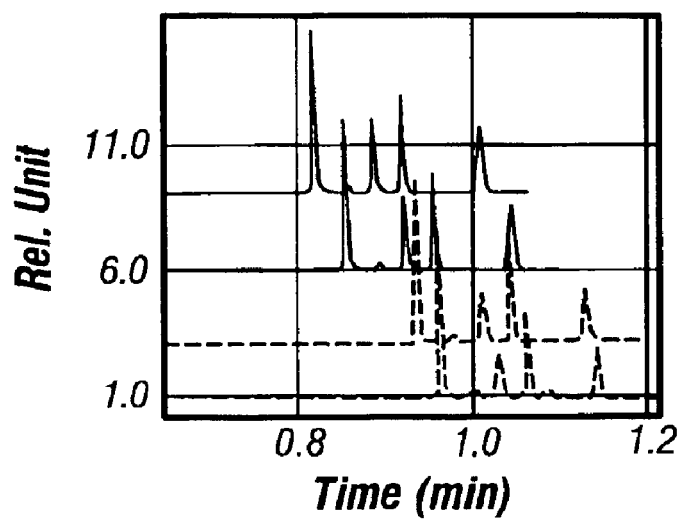
FIG. 13 shows an eTag™ probe separation using an electrode-integrated plastic chip in accordance with the present invention.

FIG. 13 shows the electrophoretic separation of four eTag™ probes using electrodes integrated onto plastic microchips. The results from control experiments are shown for comparison. Two electropherograms in the same channel show good reproducibility of the separation and the two electropherograms in dashed line at the bottom are the results from control experiments where platinum wires were used as driving electrodes. A mixture of four probes, each at 2.5 nM concentration, was added to the sample well. The electric field strength for the separation is 400 V/cm. These data indicate that the separations using patterned electrodes are essentially identical to those obtained using external platinum wire electrodes.

We also performed electrophoretic separations for larger numbers of eTag probes. Larger number of eTag probes would enable more highly multiplexed assays. Separation results for 13 eTag™ probes were obtained using control chips (external electrodes) and electrode-integrated chips made in accordance with the present invention. The devices were put together as follows: an ink electrode was screen printed on the polymer film first and then laminated to a substrate having channels and reservoirs. Alignment during the lamination assures the ink electrodes were placed in the reservoirs as indicated in FIG. 1.

Figure 14A:
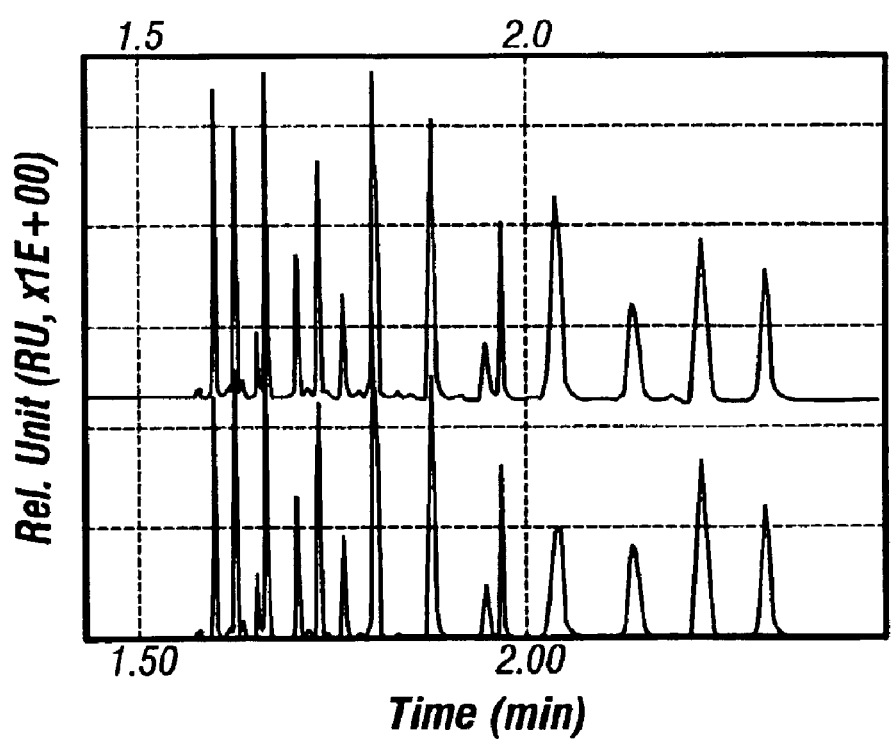
FIG. 14A shows separation data of 13 eTag™ probes using a carbon ink electrode integrated on a plastic chip in accordance with the present invention. The lower electropherogram is data from a control experiment where platinum wires were used as driving electrodes in the same reservoirs as the integrated electrodes.
Figure 14B:
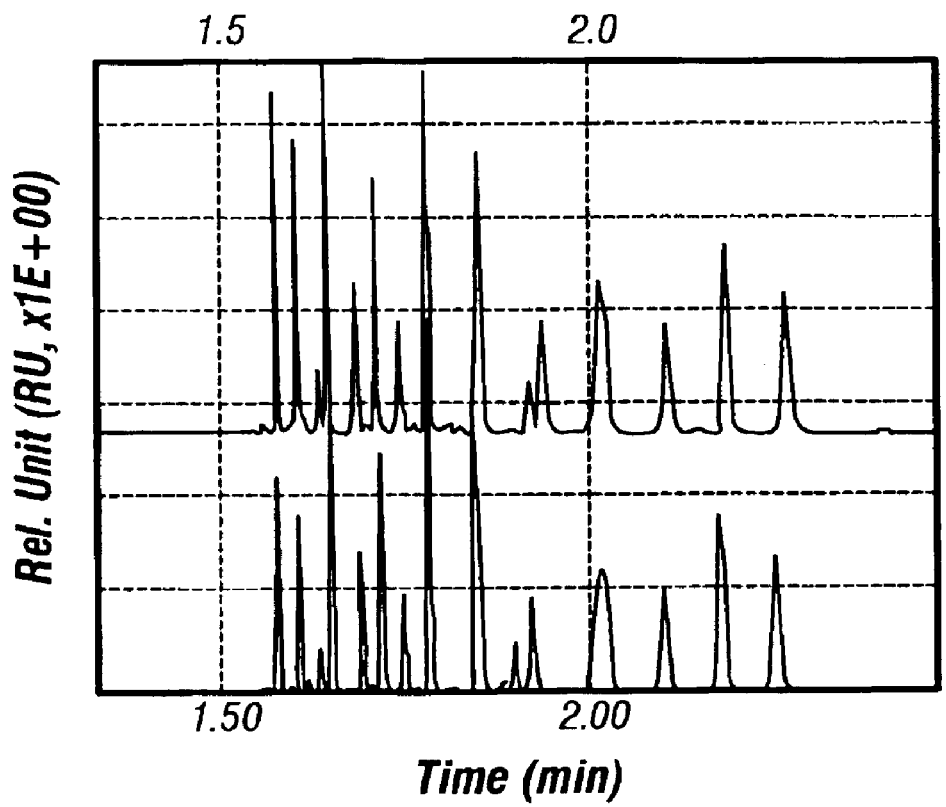
FIG. 14B shows separation data of 13 eTag™ probes using an Ag/AgCl ink electrode integrated on a plastic chip in accordance with the present invention. The lower electropherogram is data from a control experiment where platinum wires were used as driving electrodes in the same reservoirs as the integrated electrodes.

These results are given in FIGS. 14A and 14B and Tables 2 and 3. Results from control experiments in the same channel and different channel are also given for comparison. All 13 eTag™ probes are well separated on both chips with similar full width half maximum (FWHM) and resolution as that using external control Pt wires. However, the coefficients of variation (CV) on both carbon ink and Ag/AgCl ink, especially Ag/AgCl ink integrated electrodes are improved, suggesting the reliable and reproducible separation of multiple e-Tag probes can be achieved using integrated ink electrodes. These results can be contributed to less bubble generation on carbon ink and no bubble generation on Ag/AgCl ink during the electrophoretic separations.

TABLE 2

| eTag™ Probes (-FC) | Average | | | CV | | |
|---|---|---|---|---|---|---|
| | Control* | C-ink** | C-ink*** | Control* | C-ink** | C-ink*** |
| | Migration Time (min) | | | | | |
| 163 | 1.58 | 1.59 | 1.60 | 0.58 | 0.29 | 0.57 |
| 158 | 1.61 | 1.62 | 1.62 | 0.50 | 0.29 | 0.63 |
| 33 | 1.65 | 1.66 | 1.67 | 0.46 | 0.30 | 0.67 |
| 26 | 1.69 | 1.70 | 1.71 | 0.44 | 0.32 | 0.72 |
| 25 | 1.72 | 1.72 | 1.73 | 0.47 | 0.31 | 0.78 |
| 174 | 1.75 | 1.76 | 1.77 | 0.49 | 0.34 | 0.84 |
| 1 | 1.78 | 1.80 | 1.81 | 0.53 | 0.36 | 0.86 |
| 187 | 1.86 | 1.87 | 1.88 | 0.64 | 0.40 | 0.97 |
| 188 | 1.94 | 1.96 | 1.98 | 0.89 | 0.43 | 1.14 |
| 189 | 2.02 | 2.04 | 2.05 | 0.55 | 0.33 | 1.03 |
| 190 | 2.11 | 2.13 | 2.15 | 0.76 | 0.45 | 1.27 |
| 191 | 2.19 | 2.22 | 2.24 | 0.79 | 0.49 | 1.40 |
| 192 | 2.27 | 2.30 | 2.32 | 0.90 | 0.52 | 1.48 |
| | Normalized peak height (vs. 192FC) | | | | | |
| 163 | 2.09 | 2.24 | 2.22 | 1.06 | 3.56 | 3.45 |
| 158 | 1.85 | 1.94 | 1.93 | 2.74 | 3.68 | 2.92 |
| 33 | 2.38 | 2.49 | 2.47 | 3.35 | 3.83 | 3.13 |
| 26 | 0.95 | 1.04 | 1.04 | 5.75 | 6.20 | 5.13 |
| 25 | 1.72 | 1.77 | 1.76 | 1.85 | 0.58 | 2.24 |
| 174 | 0.72 | 0.75 | 0.75 | 2.31 | 3.85 | 3.76 |
| 1 | 2.53 | 2.57 | 2.58 | 2.69 | 4.15 | 4.01 |
| 187 | 1.93 | 1.99 | 2.01 | 3.07 | 4.57 | 4.62 |
| 188 | 0.97 | 1.01 | 0.95 | 29.79 | 27.05 | 34.77 |
| 189 | 0.99 | 1.26 | 1.34 | 26.34 | 25.44 | 16.58 |
| 190 | 0.72 | 0.73 | 0.74 | 2.07 | 4.89 | 8.24 |
| 191 | 1.27 | 1.27 | 1.27 | 1.07 | 3.04 | 4.07 |
| 192 | 1 | 1 | 1 | | | |
| | Half-peak width(s) | | | | | |
| 163 | 0.18 | 0.18 | 0.18 | 7.76 | 1.08 | 1.90 |
| 158 | 0.19 | 0.20 | 0.20 | 3.83 | 1.03 | 2.49 |
| 33 | 0.23 | 0.23 | 0.24 | 4.73 | 0.87 | 2.54 |
| 26 | 0.28 | 0.28 | 0.29 | 5.99 | 0.80 | 3.73 |
| 25 | 0.25 | 0.27 | 0.28 | 9.96 | 5.66 | 2.87 |
| 174 | 0.29 | 0.30 | 0.30 | 3.54 | 1.20 | 2.62 |
| 1 | 0.34 | 0.36 | 0.37 | 3.19 | 1.27 | 2.81 |
| 187 | 0.38 | 0.40 | 0.41 | 3.90 | 0.86 | 3.22 |
| 188 | 0.32 | 0.34 | 0.37 | 28.27 | 19.5 | 25.88 |
| 189 | 1.18 | 0.95 | 0.89 | 29.76 | 30.94 | 16.95 |
| 190 | 0.68 | 0.74 | 0.76 | 1.55 | 7.81 | 14.25 |
| 191 | 0.65 | 0.73 | 0.75 | 3.20 | 8.39 | 10.29 |
| 192 | 0.69 | 0.75 | 0.77 | 3.95 | 5.18 | 6.38 |
| | Resolution | | | | | |
| 163 | | | | | | |
| 158 | 2.47 | 2.51 | 2.48 | 2.74 | 2.48 | 1.95 |
| 33 | 3.50 | 3.55 | 3.10 | 11.21 | 12.04 | 2.99 |
| 26 | 3.02 | 3.06 | 2.75 | 10.50 | 8.22 | 2.00 |
| 25 | 1.70 | 1.68 | 1.82 | 3.23 | 3.00 | 11.04 |
| 174 | 2.04 | 2.06 | 2.23 | 2.03 | 0.82 | 14.01 |
| 1 | 2.37 | 2.29 | 2.30 | 4.83 | 0.20 | 1.33 |
| 187 | 3.46 | 3.20 | 3.13 | 8.09 | 1.27 | 1.81 |
| 188 | 3.29 | 3.47 | 3.60 | 17.6 | 5.09 | 2.62 |
| 189 | 2.09 | 1.91 | 2.11 | 14.0 | 6.63 | 3.06 |
| 190 | 2.19 | 2.23 | 2.44 | 1.02 | 6.95 | 9.56 |
| 191 | 2.44 | 2.39 | 2.40 | 4.20 | 2.67 | 2.78 |
| 192 | 2.05 | 1.99 | 1.98 | 6.48 | 2.85 | 2.55 |

13-eTag™-probe separation with control chip and carbon ink electrode-integrated chip. The first column shows the speciic eTag™ probes used for the separation. The concentration of eTag™ probes is from 4 to 49 nM. The separation field strength is 400 V/cm.

TABLE 2-continued

| eTag ™ Probes (-FC) | Average | | | CV | | |
|---|---|---|---|---|---|---|
| | Control* | C-ink** | C-ink*** | Control* | C-ink** | C-ink*** |

*Average of 3 control experiments on the same channel
**Average of 3 integrated-electrode-card on the same channel
***Average of integrated-electrode-card on 3 different channels.

Migration time: The time it takes after sample injection for the analyte peak to reach the detection point.

Half-peak width: The width of the peak at half its maximum height

Normalized peak height: The peak height of each peak is divided by the height of one certain peak (in this case, the last eluted peak), the calculated peak height is termed as Normalized Peak Height.

Resolution: The resolution provides a quantitative measure of its ability to separate two analytes. It is defined as the difference between the migration time of two adjacent peaks divided by the sum of the half-peak width of these peaks.

$$R_s = (t_B - t_A)/(W_{1/2B} - W_{1/2A})$$

$R_s$: Resolution t: Migration time $W_{1/2}$: Half-Peak width

A&B are two adjacent peaks

Control: the experiments using external platinum wires as driving electrodes for the CE separation.

C: the experiments using carbon ink electrodes as driving electrodes for the CE separation.

TABLE 3

| eTag ™ Probes (-FC) | Average | | CV | |
|---|---|---|---|---|
| | Control* | Ag/AgCl Ink** | Control* | Ag/AgCl Ink** |
| Migration time (min) | | | | |
| 163 | 1.58 | 1.58 | 0.80 | 0.44 |
| 158 | 1.61 | 1.61 | 0.84 | 0.47 |
| 33 | 1.65 | 1.65 | 0.72 | 0.46 |
| 26 | 1.69 | 1.69 | 0.73 | 0.49 |
| 25 | 1.72 | 1.72 | 0.84 | 0.50 |
| 174 | 1.75 | 1.75 | 0.88 | 0.49 |
| 1 | 1.78 | 1.79 | 0.95 | 0.51 |
| 187 | 1.86 | 1.86 | 1.11 | 0.55 |
| 188 | 1.94 | 1.95 | 1.61 | 0.61 |
| 189 | 2.02 | 2.03 | 0.64 | 0.50 |
| 190 | 2.12 | 2.12 | 1.34 | 0.59 |
| 191 | 2.20 | 2.20 | 1.52 | 0.66 |
| 192 | 2.27 | 2.28 | 1.66 | 0.69 |
| Normalized peak height (vs. 192FC) | | | | |
| 163 | 1.80 | 2.30 | 14.69 | 3.08 |
| 158 | 1.57 | 1.98 | 17.77 | 3.20 |
| 33 | 2.12 | 2.50 | 12.70 | 2.96 |
| 26 | 0.92 | 1.02 | 8.27 | 2.85 |
| 25 | 1.70 | 1.74 | 3.84 | 3.78 |
| 174 | 0.71 | 0.74 | 3.31 | 2.26 |
| 1 | 2.53 | 2.51 | 3.21 | 2.43 |
| 187 | 1.94 | 1.94 | 3.55 | 1.65 |
| 188 | 0.74 | 0.75 | 7.32 | 3.00 |
| 189 | 0.92 | 1.12 | 13.89 | 14.0 |

TABLE 3-continued

| eTag ™ Probes (-FC) | Average | | CV | |
|---|---|---|---|---|
| | Control* | Ag/AgCl Ink** | Control* | Ag/AgCl Ink** |
| 190 | 0.68 | 0.76 | 7.89 | 6.44 |
| 191 | 1.24 | 1.30 | 3.09 | 2.12 |
| 192 | 1 | 1 | | |
| Half-peak width(s) | | | | |
| 163 | 0.17 | 0.18 | 13.24 | 2.20 |
| 158 | 0.20 | 0.19 | 5.713 | 1.74 |
| 33 | 0.24 | 0.23 | 3.037 | 1.53 |
| 26 | 0.29 | 0.28 | 13.08 | 2.26 |
| 25 | 0.26 | 0.27 | 4.03 | 2.77 |
| 174 | 0.29 | 0.29 | 3.15 | 1.72 |
| 1 | 0.34 | 0.35 | 4.88 | 1.40 |
| 187 | 0.39 | 0.39 | 5.17 | 1.52 |
| 188 | 0.41 | 0.41 | 4.62 | 2.89 |
| 189 | 1.046 | 1.02 | 18.54 | 19.18 |
| 190 | 0.76 | 0.68 | 10.06 | 9.14 |
| 191 | 0.68 | 0.66 | 5.89 | 4.44 |
| 192 | 0.72 | 0.71 | 6.34 | 2.99 |
| Resolution | | | | |
| 163 | | | | |
| 158 | 2.26 | 2.24 | 14.68 | 18.68 |
| 33 | 2.84 | 2.74 | 34.08 | 24.12 |
| 26 | 2.53 | 2.62 | 13.45 | 10.16 |
| 25 | 1.63 | 1.68 | 8.24 | 1.44 |
| 174 | 2.04 | 2.04 | 0.73 | 1.51 |
| 1 | 2.31 | 2.32 | 1.28 | 0.82 |
| 187 | 3.30 | 3.20 | 5.71 | 0.61 |
| 188 | 3.56 | 3.48 | 6.56 | 5.46 |
| 189 | 2.17 | 2.05 | 6.27 | 6.80 |
| 190 | 2.55 | 2.34 | 25.62 | 13.38 |
| 191 | 2.39 | 2.42 | 3.73 | 1.03 |
| 192 | 2.06 | 2.04 | 4.70 | 3.37 |

13-eTag ™-probe separation with control chip and Ag/AgCl ink electrode-integrated chip. The first column shows the specific eTag ™ probes used for the separation. The concentration of eTag ™ probes is from 4 to 40 nM. The separation field strength is 400 V/cm.
*: Average of control experiments on 3 different channels
**: Average of integrated-electrode-card on 3 different channels Field Strength Test Using Ink-integrated Labcard In our previous work, we found that by using Ag/AgCl ink electrodes, the bubble generation was eliminated. We further performed field strength experiments to determine whether we could increase the field strength without generating bubbles. The field strength applied on Ag/AgCl ink electrodes was increased to 600 V/cm without much variation, however, if the field strength in the control experiments (using Pt wires as driving electrodes) was increased to 600 V/cm, huge variation was observed in most of the parameters; the current was very unstable due to the bubble generation and sometimes caused failure of the separation.

Figure 23:
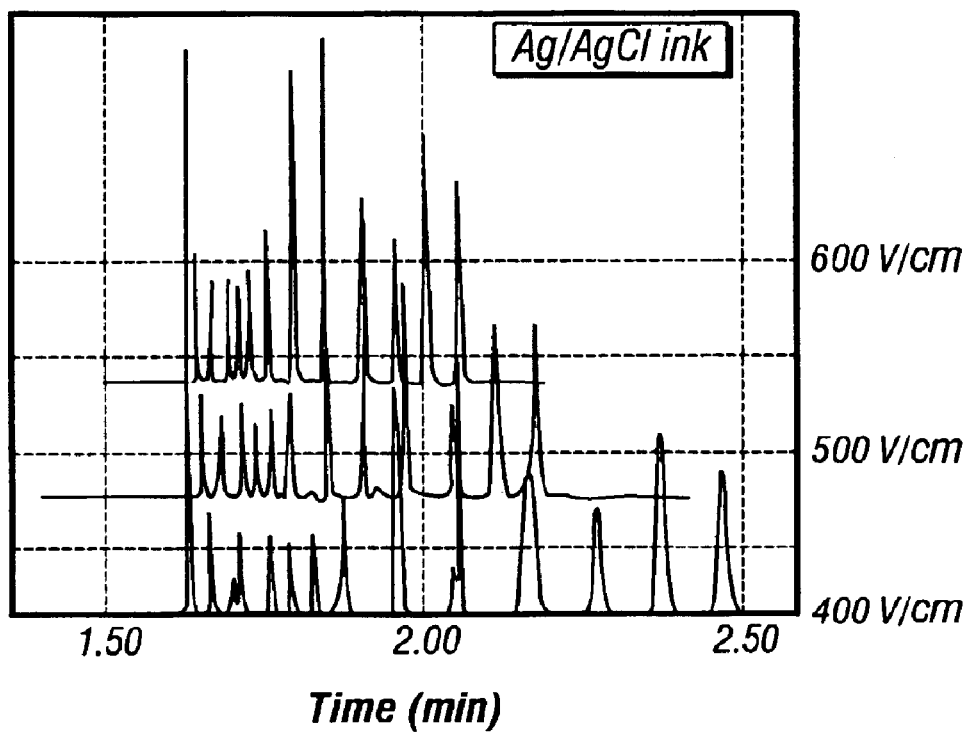
FIG. 23 shows data for a separation of 13 eTag probes on a microfluidic device integrated with Ag/AgCl ink electrodes. The field strength was increased from 400 V/cm (bottom) to 600 V/cm (top).

As indicated in FIG. 23, the increase of the field strength resulted in faster separation, higher separation efficiency and acceptable resolution.

Figure 24A:
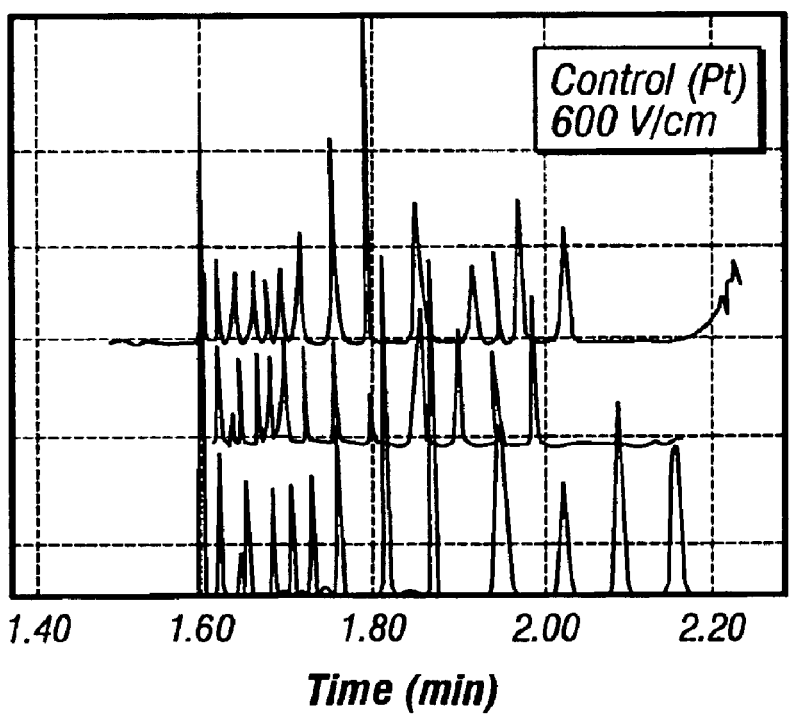
FIG. 24A shows data for a separation of 13 eTag probes on a microfluidic device using platinum wires as external driving electrodes. The field strength was 600 V/cm.

In the control experiments in which platinum wires were used as external driving electrodes for the separation, when the field strength was increased to 600 V/cm, huge variation was observed between different runs. This is evidenced by FIG. 24A which shows 3 different runs. The variation is large despite each run being carried out in a first-use channel. Good separation could not be achieved due to the unstable current probably caused by the generation of bubbles under higher field strength.

Figure 24B:
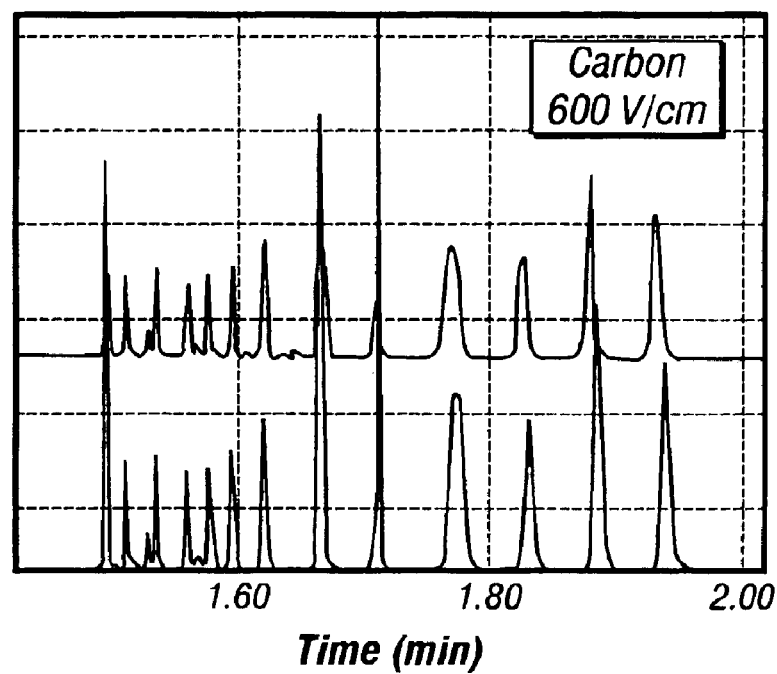
FIG. 24B shows data for a separation of 13 eTag probes on a microfluidic device integrated with carbon ink electrodes. The separation strength is 600 V/cm.
Figure 24C:
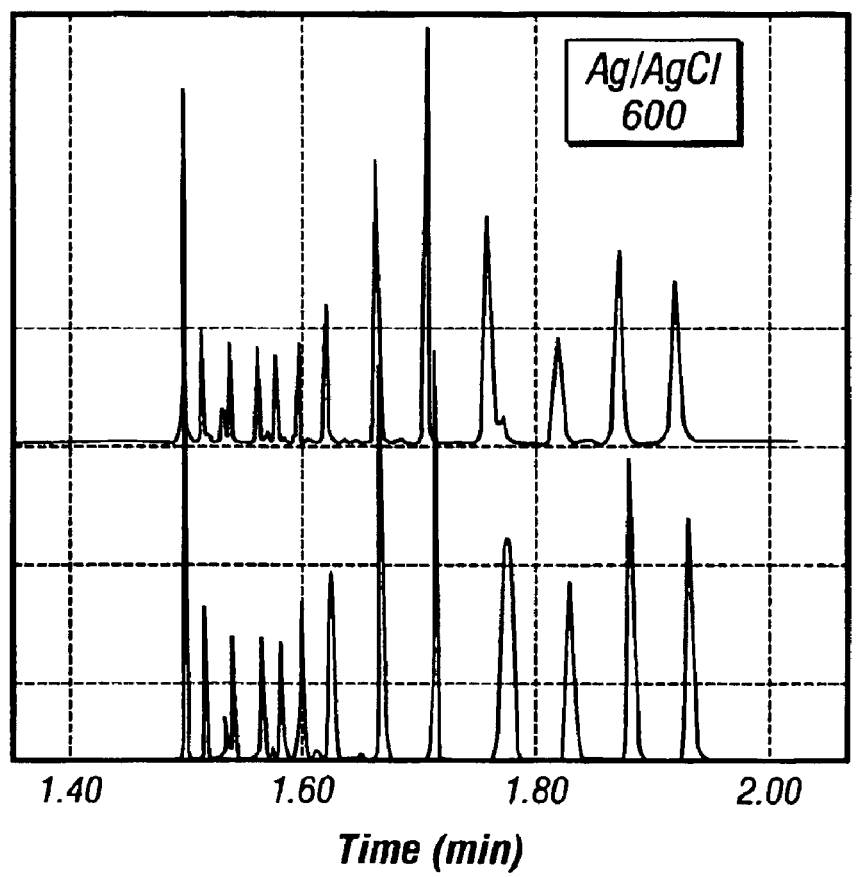
FIG. 24C shows a separation of 13 eTag probes on a microfluidic device integrated with Ag/AgCl ink electrodes. The separation strength is 600 V/cm.

FIG. 24C shows data for two different runs for Ag/AgCl ink electrode integrated on a microfluidic device or labcard made in accordance with the present invention. FIG. 24B also shows two different runs for carbon ink electrode integrated on a labcard in accordance with the present invention. The data shown in FIGS. 24B and 24C indicates that ink electrodes inhibit bubble formation in such a degree that higher field strengths may be applied.

FIG. 25 illustrates a summary chart for the field strength test (600 V/cm) using Ag/AgCl-ink-integrated microfluidic devices.

The above referenced data indicates that integrated ink electrodes are as reliable as control platinum wires or Au pins. The ink integrated electrodes are comparable to the control methods and perform better than "conventional" control methods in which platinum wires are positioned manually using tape. We believe automation of the integrated ink electrodes would further improve the performance of the tested ink-integrated electrode devices. Additionally, we found that use of the integrated Ag/AgCl ink electrodes made it possible to increase the separation field strength up to 600 V/cm without decreasing separation performance. We attribute this result to the ink electrodes' ability to reduce bubble formation.

Ink Coated Electrodes

We built and tested microdevices using "dropped in" ink coated electrodes. The electrodes were used to electrokinetically drive materials through channels in the devices. Each device comprised a plastic substrate having interconnected microchannels and a cover thermally bonded to the substrate. The devices did not include integrated electrodes. Instead, ink coated wire electrodes were deployed in the reservoir and made electrical contact with the medium contained therein. The medium utilized in these tests was 15 mM pH 8 sodium phosphate +1% PEO.

Figure 15A:
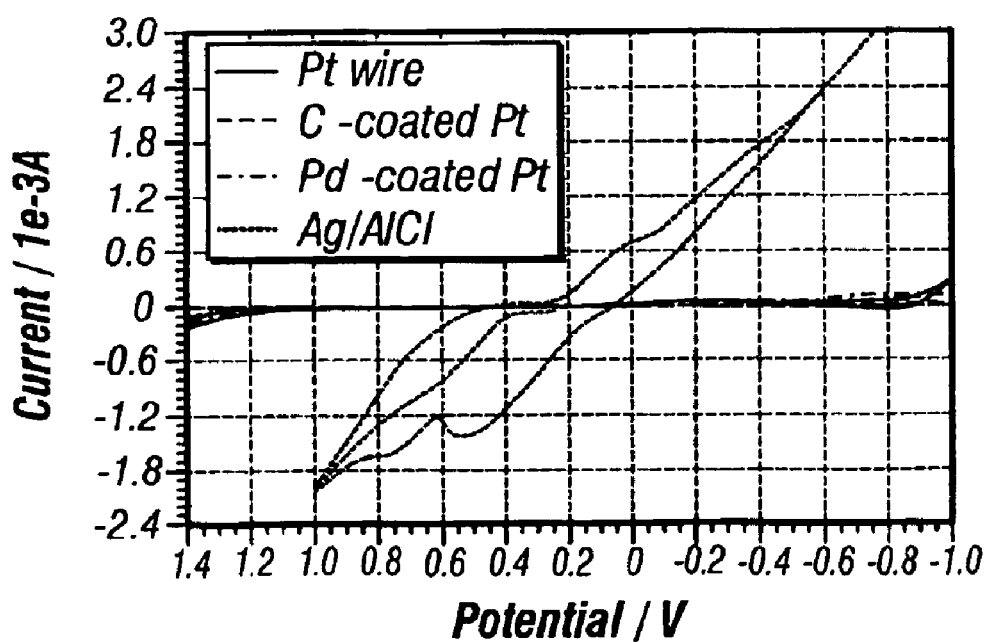
FIGS. 15A and 15B show graphical illustrations of cyclic voltammetry data of platinum wire, carbon ink-, 20% Pd doped carbon ink-, Ag/AgCl ink-coated platinum wires in a buffer solution (pH=8.0) using a scan rate of 100 mV/s. The reference electrode is Ag/AgCl and the counter electrode is a platinum wire.
Figure 15B:
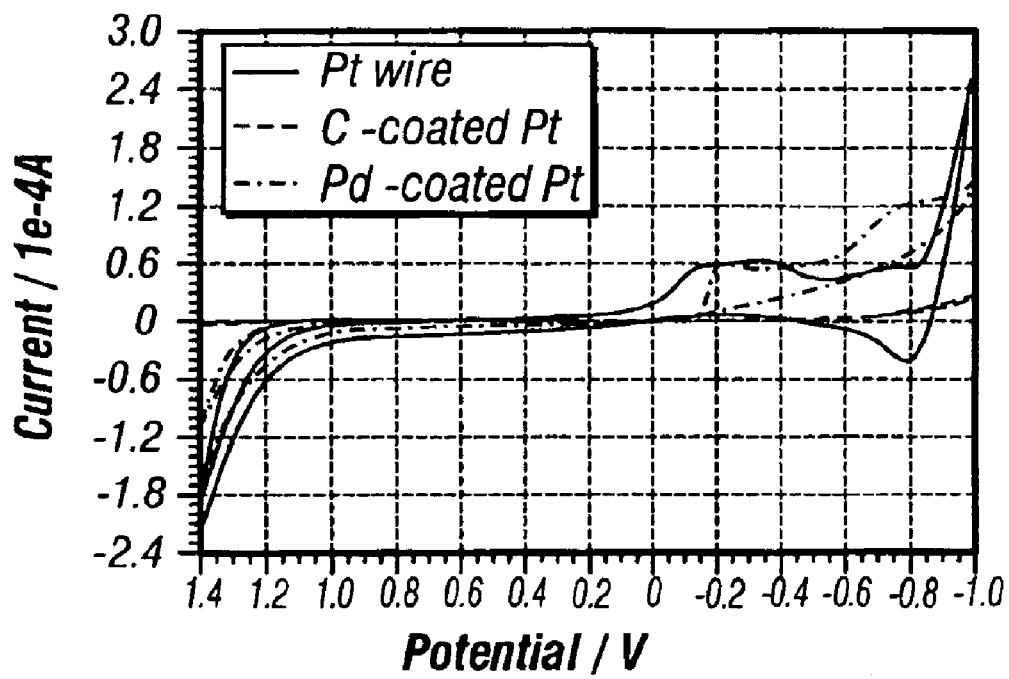

FIGS. 15A and 15B indicate significant oxidation and reduction current is present on platinum wires when the potential is higher than 1.0 V or lower than −0.8 V (vs. Ag/AgCl. 3M NaCl), which corresponds to the oxidation of water to $O_2$ and the reduction of water to $H_2$. This follows from the observation that bubbles are formed at certain potentials. Such potentials are typical during CE separation.

However, we did not see significant oxidation and reduction of the water on carbon ink-coated Pt wire at the same potential levels. This was evidenced by the lack of bubbles. On the Pd-doped carbon electrode, we observed the suppression of gas bubble formation on the electrode.

The voltammogram on Ag/AgCl ink behaves different from that on platinum wire; higher oxidation or reduction current results at a much lower anode potential or much higher cathode potential. This is due to the oxidation of the Ag and the reduction of $Ag^+$ in the ink. Therefore, either an ink-integrated microchip or an ink-coated external electrode can be used as driving electrode for electrokinetic separations with less bubble generation than typical non-ink electrodes.

Figure 16:
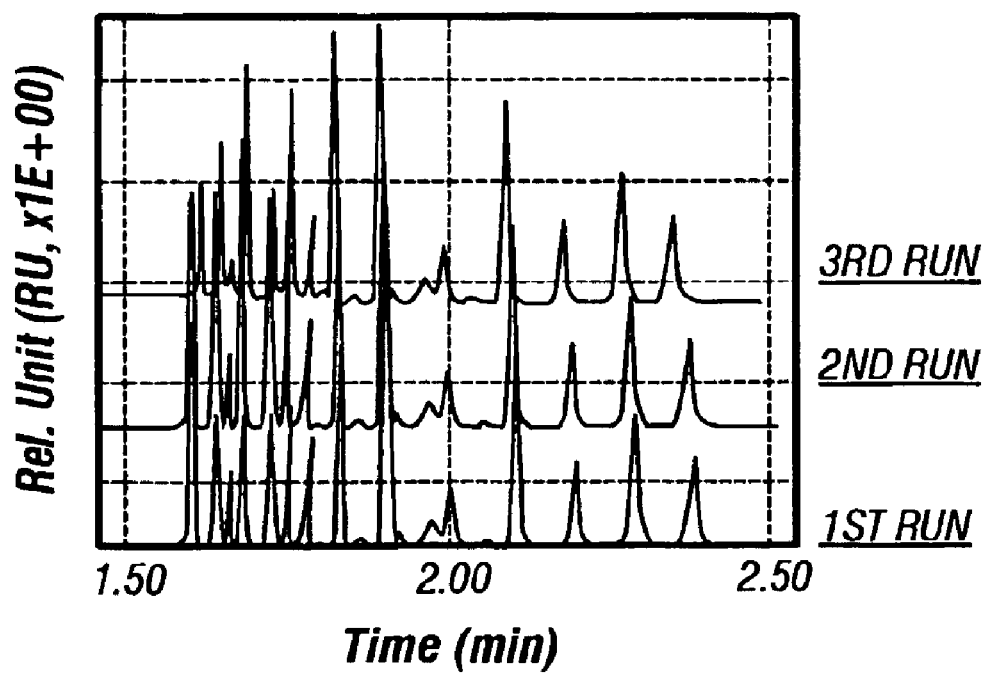
FIG. 16 shows separation of 13 eTag™ probes using carbon-ink-coated platinum wires as driving electrodes in accordance with the present invention.
Figure 17:
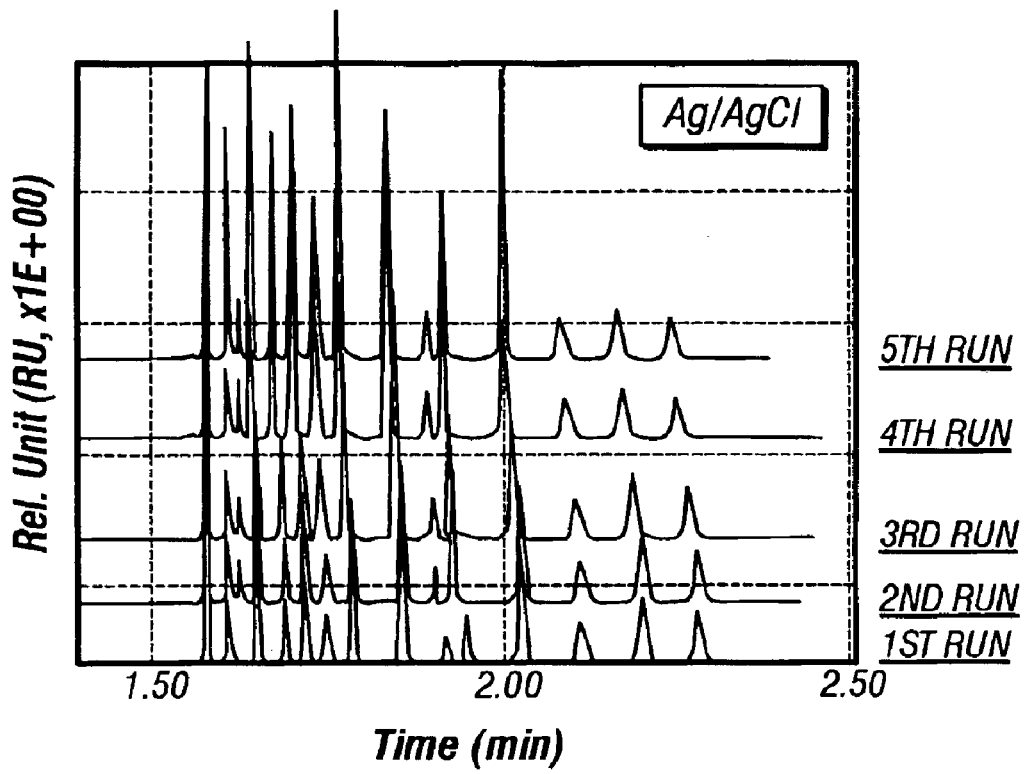
FIG. 17 shows separation of 13 eTag™ probes using Ag/AgCl-ink-coated platinum wires as driving electrodes in accordance with the present invention.

FIGS. 16 and 17 show the results of on-chip electrophoretic separations of 13 e-Tag probes using carbon ink-coated Pt electrodes and Ag/AgCl ink-coated Pt electrode respectively. If the coating process is controlled well (i.e., amongst other processing conditions the thickness and uniformity are consistent and thorough), the coated electrodes will provide a surprisingly good separation performance as shown in FIGS. 16 and 17. FIGS. 16 and 17 indicate that carbon-ink coated Pt wires can be used as driving electrode for at least three consecutive runs and Ag/AgCl ink coated Pt wires may be used for at least 5 consecutive runs without significant effect on the separation performance. Few bubbles were observed on carbon-ink coated electrodes and no bubbles were observed on Ag/AgCl ink coated electrodes. In contrast, it is hard to achieve consecutive runs using bare platinum wires because of the bubble generation.

Integrated Heating

Heaters consisting of electrically-conducting ink traces having different dimensions (from 0.25 mm to 4 mm) were prepared on plastic in accordance with the present invention. They responded rapidly to the application and removal of power. The heating component was applied as a thin ink trace on a plastic substrate in various patterns such as simple strips or in a meandering "square-wave" pattern. See, for example, FIGS. 6C, 8 and 9. Both simple strips and serpentine or square-wave patterns can meet the requirements for many applications.

Figure 18:
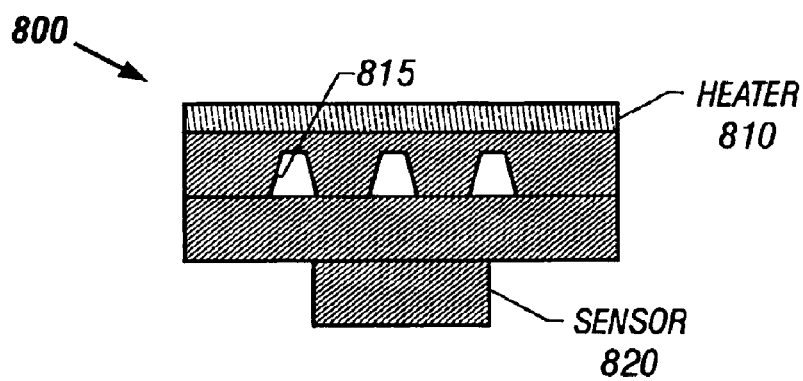
FIG. 18 shows a cross sectional view of another microfluidic device having an integrated heater in accordance with the present invention.

FIG. 18 shows device 800 with an integrated heater 810. In this case a heater 810 was placed outside of the microchannels 815, and a temperature sensor 820 was attached to the opposite side of device 800, across the substrate and channels from heater 810. The heating element 810 was thus not in fluid communication with the channels 815. Results for various heating elements are provided in FIGS. 19–21 (FIGS. 19A and 19B corresponding to metallic heaters and FIGS. 20A to 21C corresponding to ink heaters).

Figure 19:
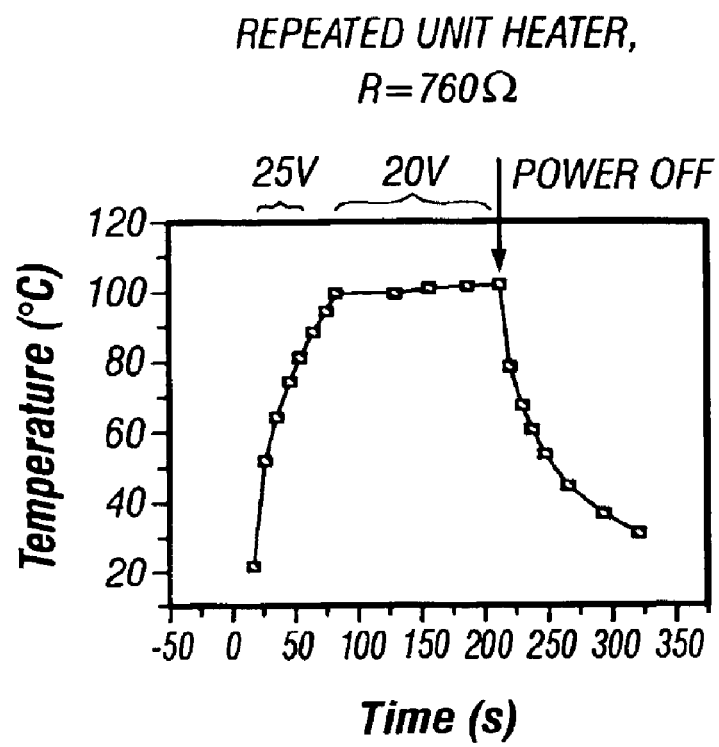
FIG. 19 shows thermal response as a function of time for an applied voltage of 20 V of an integrated ink electrode heater on a microfluidic chip in accordance with the present invention. The heater features a serpentine shape.
Figure 20:
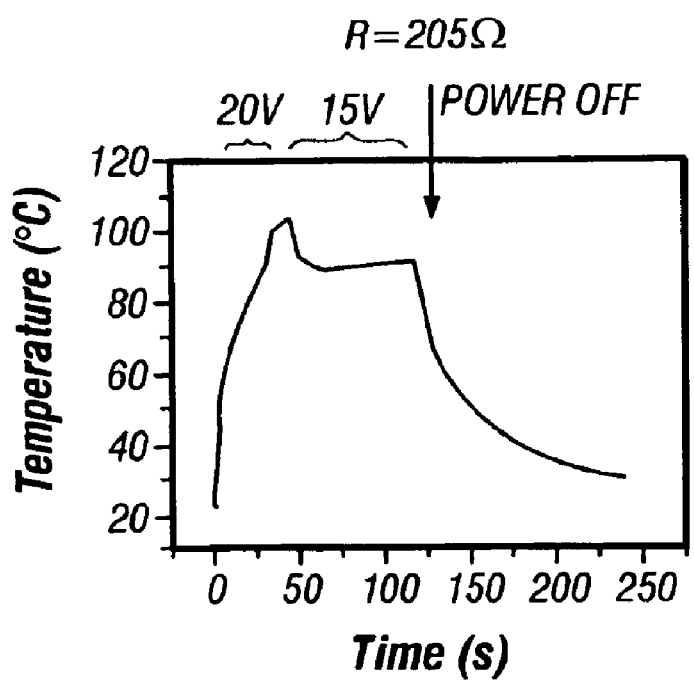
FIG. 20 shows thermal response as a function of time for an applied voltage of 15 V of an integrated ink electrode heater on a microfluidic chip in accordance with the present invention. The heater is a single strip trace of 84.5×1×0.030 mm.

FIGS. 19 and 20 show experimental results of a serpentine-shape (resistance=760 ohms) and linear strip shape (resistance=205 ohms) electrode heaters respectively. In each case, the temperature increased sharply within about the first 50 seconds upon application of 20–25 volts and remained relatively constant until the power was turned off. This data indicates that the electrically conducting ink electrodes of the present invention have a quick thermal response upon application of a voltage. This data also indicates the heating elements can hold a temperature constant while voltage is applied at a constant level. Indeed, both FIGS. 19 and 20 show a relatively constant temperature after 50 seconds until the power is turned off.

Figure 21A:
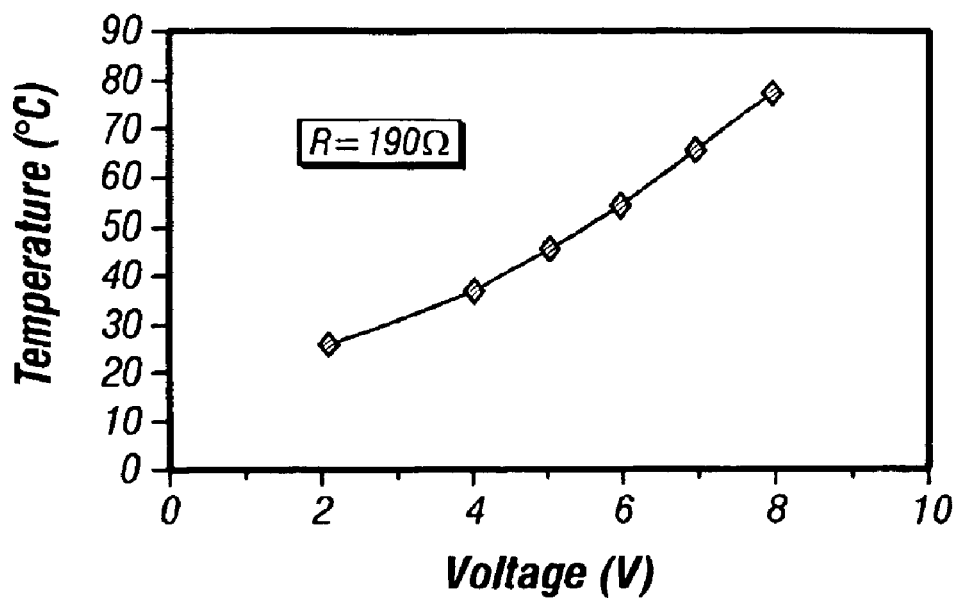
FIGS. 21A and 21B show thermal response as a function of voltage and resistance respectively of an integrated ink electrode heater on a microfluidic device in accordance with the present invention. The heater is a single strip.

FIG. 21A shows the thermal response of yet another integrated heater made of a single strip electrically conducting ink having a resistance of 190 Ω at room temperature. FIG. 21A indicates the local temperature depends on applied voltage.

Figure 21B:
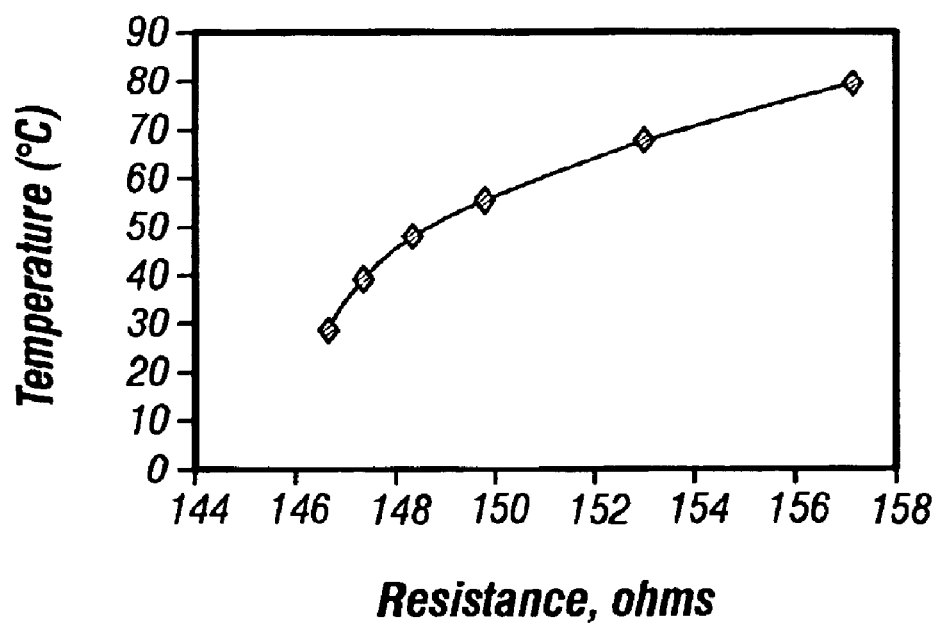

FIG. 21B shows temperature of the electrode as a function of resistance. A review of this data indicates the heater resistance is proportional to the temperature. Thus the heater itself can be used as a probe for temperature sensing by monitoring the resistance change during the experiment.

Figure 21C:
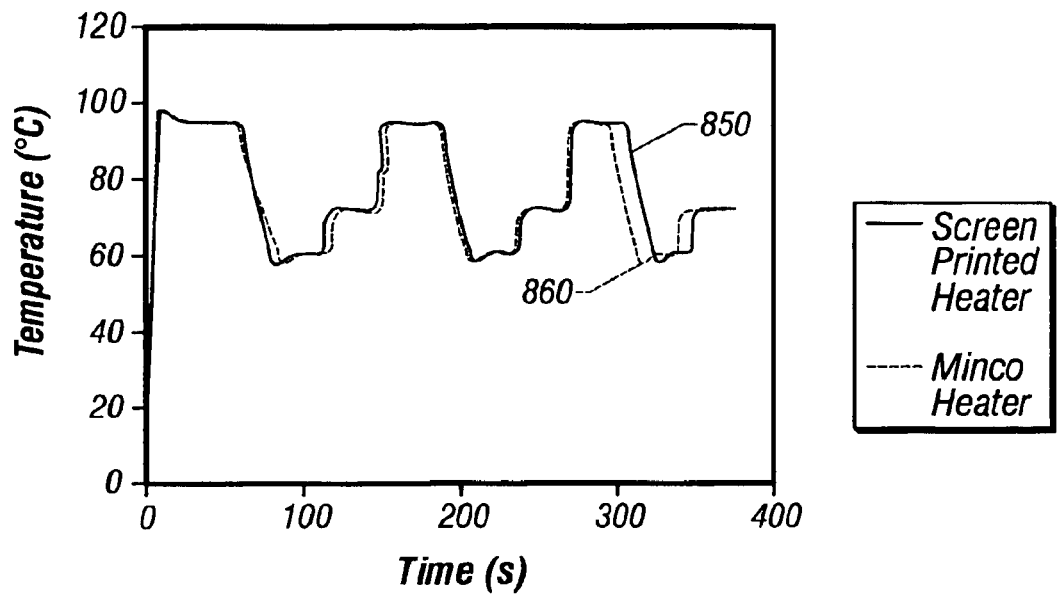
FIG. 21C shows thermal cycling of screen printed heaters on plastic chip in accordance with the present invention and a commercial heat strip.

Cyclic testing was also carried out on various heating elements of the present invention. That is, voltage was increased and decreased periodically to determine cyclic performance of an electrically conducting ink electrode, FIG. 21C shows the thermal cycling for PCR using ink screen printed heaters on a plastic chip. A commercial heat strip was also tested for comparison purposes. Reference numerals 850 and 860 correspond to the ink and metal electrodes respectively. Both electrodes were raised to 95° C. for 45 s; 61° C. for 30 s; and 72° C. for 45 s. This data indicates the commercial metal heat strips and the electrically conducting ink electrodes of the present invention behave similarly.

It follows that the applied voltage can be programmed to obtain other response schemes (even faster responses) to changes in power. This heat cycling may be useful in PCR and other various thermal operations. Additionally, the on-chip heaters of the present invention may be used for, but not limited to, capture/realease of biomolecule on a specific location, as a pump to move fluids in the channel network, as valve by combining with thermal sensetive gel or other materials, or for separation of different sized particals.

Figure 22A:
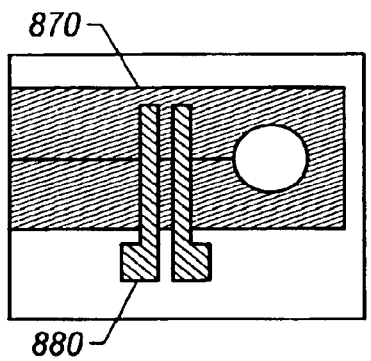
FIGS. 22A and 22B show partial top and cross sectional views respectively of a microfluidic device having an integrated chemical sensor in accordance with the present invention.
Figure 22B:
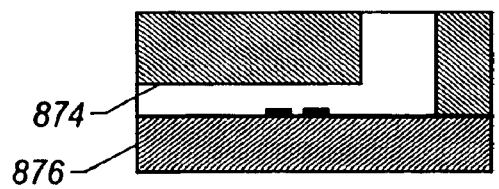

Electrically conducting ink electrodes can also be used as a on-chip electrochemical detector as shown in FIGS. 22A and 22B. At least one electrode 870, connected via contact pad 880, may be positioned in the channel 874 and in contact with the subject sample. For example $Cu_2O$-doped carbon ink can be patterned on a cover 876 and used as working electrode to detect carbohydrate, amino-acid. The counter and reference electrodes can be also prepared on the chip.

From the above results and discussion, many advantages of the claimed invention become readily apparent. The claimed invention provides for an integrated microdevice for analytical and research purposes comprised of a plastic material. This leads to many benefits such as low cost, numerous options for manufacturing processes, disposability, and the like. More particularly, the claimed invention provides for a substrate, suitable for chemical applications, that may have an unmodified natural surface to which conductive films may be applied in various patterns. In some exemplary configurations of the present invention, the electrically conducting film patterns are strongly adherent. This distinctive property may be particularly suitable in some instances where surface chemistries present on the substrates of the device interfere with sensitive chemical operations. For instance, where the device of interest involves channels for electrophoretic separations, complex surface chemistries of some conventional plastics and substrate materials are generally accompanied with variations in wall surface charge. These chemistries and surface charges tend to aggravate sample adsorption to the channel walls and generate non-uniform electroosmotic flow. Because adsorption results in skewed peaks and/or no analyte migration while non-uniform electroosmotic flow causes reduced separation resolution, reliable and consistent results using modified surfaces become hard to obtain. The versatility and heat resistance of certain substrates such as norbornene based substrates enables the integration of components including, for example, an electrically conducting ink film into the subject devices.

All publications, patents and patent applications mentioned in this specification are incorporated herein by reference to the same extent as if each individual publication, patent, or patent application was specifically and individually indicated to be incorporated by reference.

The invention now being fully described, it will be apparent to one of ordinary skill in the art that many changes and modifications can be made thereto without departing from the spirit or scope of the appended claims.

All of the features disclosed in the specification (including any accompanying claims, abstract and drawings), and/or all of the steps of any method or process disclosed, may be combined in any combination, except combinations where at least some of such features and/or steps are mutually exclusive. Each feature disclosed, in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

What is claimed is:

1. A microfluidic device for operations at high field strengths comprising:

a substrate having at least one channel and at least one aperture in fluid communication with said channel;

a cover bonded to said substrate such that a reservoir is formed at said at least one aperture; and a driving electrode used to apply a field of at least 400 V/cm comprised of an electrically conducting silver/silver chloride ink pattern on at least one of said substrate and cover such that when a material is present in said channel and reservoir said ink pattern makes electrical contact with said material and such that fewer bubbles form in said channel and reservoir when establishing said field across a driving electrode of bare platinum.

2. The device of claim 1 wherein said ink pattern is on said cover.

3. The device of claim 1 wherein said electrical contact is made in said reservoir.

4. The device of claim 1 comprising a first channel, a second channel, and a third channel, the first and second channel being fluidly connected to the third channel at separate points along the third channel and wherein said electrical contact is made in one of the first channel, second channel, and third channel.

5. The device of claim 1 wherein said cover is bonded to said substrate by one method selected from the group consisting of thermal bonding, using an adhesive and using a double-sided adhesive layer.

6. The device of claim 1 wherein said material is a substance useful in electrophoretic applications.

7. The device of claim 1 wherein said ink pattern is on said substrate.

8. The device of claim 1 wherein said ink is patterned on said cover using one method selected from the group consisting of ink jet printing, screen printing and lithography.

9. The device of claim 1 wherein said cover is made of PMMA.

10. The device of claim 1 wherein said ink is an acrylic-based silver/silver chloride ink.

11. The device of claim 1 wherein said ink is a polyester based silver/silver chloride ink.

12. The device of claim 1 wherein said ink pattern has width of 10 to 400 $\mu$m.

13. The device of claim 1 wherein said ink pattern includes a contact and a lead.

14. The device of claim 1 wherein said substrate is made from a plastic selected from the group consisting of norbornene, polystyrene, acrylic, polycarbonate-polyester, and polyolefin.

15. The device of claim 1 wherein said substrate is a norbornene based substrate.

16. A method for reducing bubble formation during electrokinetic applications in a microfluidic device having interconnected channels and reservoirs, said method comprising the steps of:

providing at least two driving electrodes for contacting a medium in said channels and reservoirs when the medium is present, wherein at least one driving electrode has a surface comprising silver and silver chloride; and establishing a field of at least 400 V/cm across the at least one driving electrode having a surface comprising silver and silver chloride and another driving electrode such that fewer bubbles form in said channels and reservoirs as are formed when establishing said field across driving electrodes of bare platinum.

17. The method of claim 16 wherein said microfluidic device comprises a substrate and a cover bonded to said substrate and wherein said electrodes are integrated electrodes formed using an ink patterned on said cover such that when said cover is bonded to said substrate to form said device said ink is positioned in said reservoir and makes electrical contact with said medium therein.

18. The method of claim 16 wherein at least one of said electrodes is positioned in one of said reservoirs to make electrical contact with said medium in said reservoirs and wherein said electrode comprises a silver/silver chloride coated electrode.

19. The method of claim 17 wherein the ink is an acrylic-based silver/silver chloride ink.

20. The method of claim 17 wherein the ink comprises a polyester-based silver/silver chloride ink.

* * * * *